United States Patent [19]

Young et al.

[11] Patent Number: 4,990,526
[45] Date of Patent: Feb. 5, 1991

[54] LEUKOTRIENE ANTAGONISTS, COMPOSITIONS AND METHODS OF USE THEREOF

[75] Inventors: Robert N. Young, Senneville; Jacques-Yves Gauthier; Richard Frenette, both of Laval, all of Canada

[73] Assignee: Merck Frosst Canada, Inc., Kirkland, Canada

[21] Appl. No.: 872,309

[22] Filed: Jun. 9, 1986

Related U.S. Application Data

[63] Continuation-in-part of Ser. No. 746,203, Jun. 8, 1985, abandoned.

[51] Int. Cl.$^5$ .................. C07D 247/04; A61K 31/41; A61K 31/19; C07F 57/46
[52] U.S. Cl. ................................. 514/381; 514/419; 514/562; 514/568; 546/253; 546/252; 562/426; 562/431
[58] Field of Search ................ 562/431, 426; 548/253; 514/381, 568, 562, 419

[56] References Cited

FOREIGN PATENT DOCUMENTS 0056172 12/1981 European Pat. Off. .
0061800  3/1982 European Pat. Off. .
0068739  6/1982 European Pat. Off. .
0104885  4/1984 European Pat. Off. .
0106565  4/1984 European Pat. Off. .
0150118  7/1985 European Pat. Off. .
0168950  6/1986 European Pat. Off. .
0169033  7/1986 European Pat. Off. .
2058785  9/1979 United Kingdom .
2094301  3/1982 United Kingdom .
2128999  5/1984 United Kingdom .

Primary Examiner—David B. Springer
Attorney, Agent, or Firm—Gabriel Lopez; Hesna J. Pfeiffer

[57] ABSTRACT

Compounds having the formula:

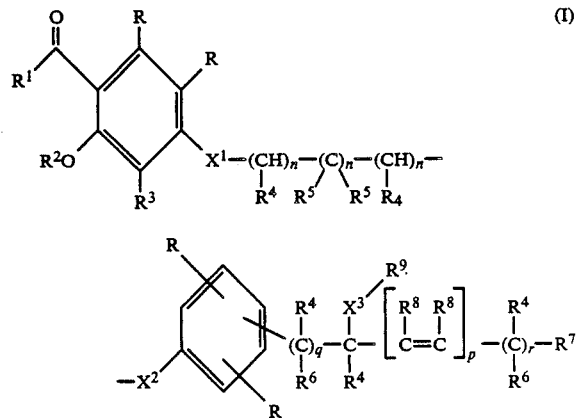

are antagonists of leukotrienes of $C_4$, $D_4$ and $E_4$, the slow reacting substance of anaphylaxis, and inhibitors of their biosynthesis. These compounds are useful as anti-asthmatic, anti-allergic, anti-inflammatory agents, anti-psoriatic agents, and cytoprotective agents.

9 Claims, No Drawings

LEUKOTRIENE ANTAGONISTS, COMPOSITIONS AND METHODS OF USE THEREOF

CROSS-REFERENCE

This is a Continuation-in-Part of U.S. Ser. No. 746,203, filed June 18, 1985, abandoned.

BACKGROUND OF THE INVENTION

This invention is directed to compounds which act as antagonists of the leukotrienes and inhibitors of their biosynthesis.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$, $D_4$ and $E_4$. These compounds collectively account for the biologically active material known as the slow reacting substance of anaphylaxis (SRS-A).

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also effects other cell types such as lymphocytes and for example may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., Ann. Rots. Med. Chem. 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. 5-lipoxygenase products are also thought to be regulators of mast cell degranulation and recent studies with human lung mast cells have suggested that 5-lipoxygenase inhibitors, but not corticosteroids, may suppress antigen-induced mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma. Leukotriene antagonists or inhibitors would therefore be a new class of drugs for the treatment of asthma.

Psoriasis is a human skin disease which effects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ and 8- and 12-HETE have been detected in psoriatic lesions, but not in uninvolved skin, in biologically significant amounts.

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, allergic conjunctivitis, gouty arthritis, and gall bladder spasms. In addition, they may have a role in cardiovascular disease because Leukotrienes $C_4$, $D_4$ and $E_4$ act as coronary and cerebral arterial vasoconstrictors and these compounds may also have negative inotropic effects on the myocardium. In addition, the leukotrienes are important mediators of inflammatory diseases through their ability of modulate leukocyte and lymphocyte function. See for example, B. Samuelson, Science, 220 568 (1983).

Several classes of compounds exhibit ability to antogonize the action of leukotrienes in mammals, especially humans. See for example: United Kingdom Patent Specification Nos. 2,058,785 and 2,094,301; and European Patent Application Nos. 56,172, 61,800 and 68,739.

DESCRIPTION OF THE INVENTION

The present invention relates to compounds having activity as leukotriene and SRS-A antagonists or inhibitors, to methods for their preparation, to intermediates useful in their preparation and to methods and pharmaceutical formulations for using these compounds in mammals (especially humans). Because of their activity as leukotriene antagonists or inhibitors, the compounds of the present invention are useful as anti-asthmatic, anti-allergic, antipsoriatic, and anti-inflammatory agents and are useful in treating allergic conjunctivitis, allergic rhinitis, and chronic bronchitis and for amelioration of skin diseases like psoriasis and atopic eczema. These compounds are also useful to antagonize or inhibit the pathologic actions of leukotrienes on the cardiovascular and vascular systems for example, actions such as result in angina. The compounds are also useful as cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The compounds of the present invention have the formula I:

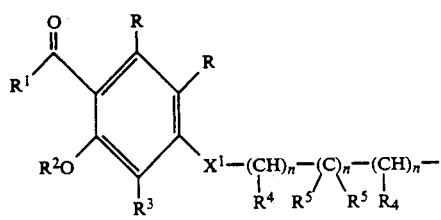

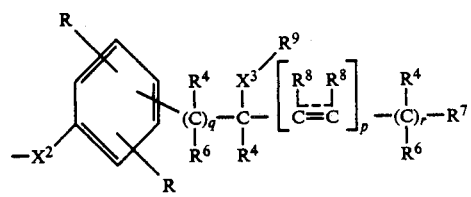

wherein:
the broken line represents an optional triple bond;
each R is independently H; OH; lower alkyl; lower alkenyl; trifluoromethyl; lower alkoxy; phenyl; phenyl substituted by alkyl of 1 to 3 carbon atoms or by halogen; benzyl; phenethyl; halogen; N(R$^4$)$_2$; —(C=O)R$^1$; CH$_2$OR$^4$; CN; SR$^{10}$; SOR$^{10}$; SO$_2$R$^{10}$; or nitro;
R$^1$ is H; lower alkyl; or lower alkoxy;
R$^2$ is H; lower alkyl; R$^4$CO; or R$^4$OCH$_2$;
each R$^3$ is independently lower alkyl or lower alkenyl;
each R$^4$ is independently H or lower alkyl;
each R$^5$ is independently H; OR$^2$; lower alkyl; or both R$^5$'s may be combined to create a doubly bonded oxygen (=O) or a =C(R$^4$)$_2$ group;
each R$^6$ is independently H; OH; or lower alkyl;
each R$^7$ is independently COOR$^4$; CHO; CH$_2$OH; tetrazole; CONHSO$_2$R$^{10}$; NHSO$_2$R$^{10}$; hydroxymethylketone; acetoxymethylketone; CON(R$^4$)$_2$; CN; Het; or

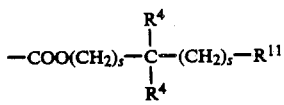

each R$^8$ is independently H or lower alkyl, and is absent when a triple bond is present;
R$^9$ is R$^3$,

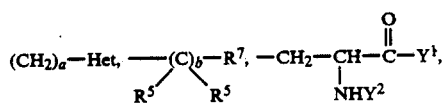

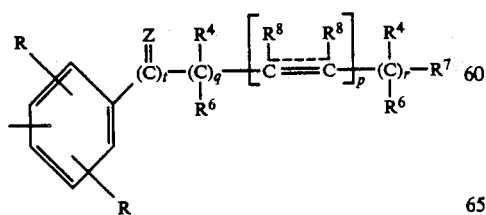

wherein the broken line represents an optional triple bond,

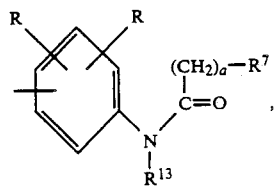

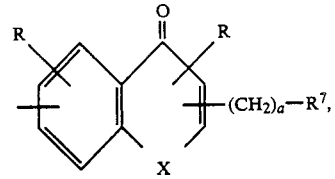

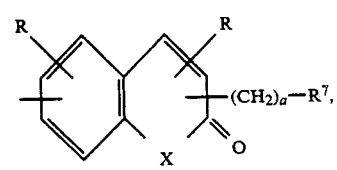

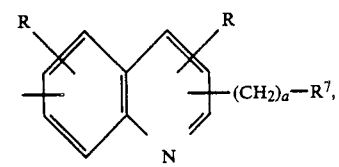

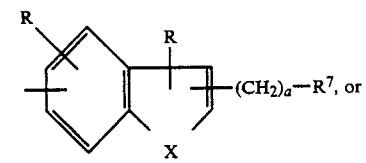

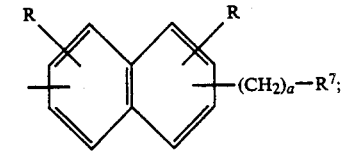

each R$^{10}$ is independently OH: N(R$^4$)$_2$; CF$_3$; lower alkyl; lower alkoxy; phenyl; or phenyl substituted by one or more alkyl or alkoxy groups of 1 to 3 carbon atoms, halogen, hydroxy, COOR$^4$, CN, formyl or lower alklacyl;
each R$^{11}$ is independently
(A) a monocyclic or bicyclic heterocyclic radical containing from 3 to 12 nuclear carbon atoms and 1 to 2 nuclear heteroatoms selected from N and S with at least one being N, and with each ring in the heterocyclic radical being formed of 5 or 6 atoms, or
(B) the radical W-R$^{12}$;
each R$^{12}$ is independently contains up to 20 carbon atoms and is (1) an alkyl radical or (2) an alkylacyl radical of an organic acyclic or monocyclic carboxylic acid containing not more than one heteroatom in the ring;
each R$^{13}$ is independently H or R$^{10}$.
each W is independently O, S or NH;
each X is independently O, S or NR$^{13}$;
X$^1$, X$^2$ and X$^3$ are each independently O, S, SO, SO$_2$, S(O)=NR$^4$, NR$^4$, NCOR$^1$, NCN, or NCONHR$^4$;

$Y^1$ is OH or the N-terminus of an amino acid such that $Y^1H$ is an essential amino acid:
$Y^2$ is H or the C-terminus of an amino acid such that $Y^2OH$ is an essential amino acid;
Z is O, H and OH, or H and $R^4$;
each a is independently 0 to 4;
each b is independently 1 to 6;
each n is independently 0 to 6;
each p is independently 0 to 2;
each q is independently 0 to 4;
each r is independently 0 to 4;
each s is independently 0 to 3;
each t is independently 0 to 1;
each Het is independently a heterocyclic or heterobicyclic ring of 5 or 6 atoms each, containing one or more heteroatoms selected from O, N or S, said heterocyclic or heterobicyclic ring containing an acidic proton;
or the pharmaceutically acceptable salts thereof.

Examples of useful heterocyclic rings (represented by Het above) include:

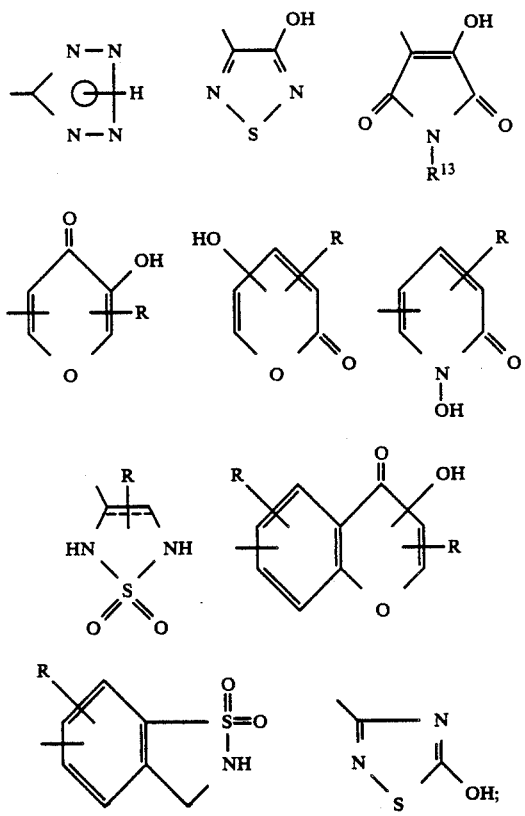

wherein the broken line represents an optional double bond.

As used herein, the term "lower alkyl" includes those alkyl groups of from 1 to 7 carbon atoms of either a straight, branched or cyclic structure. Examples of lower alkyl fragments include methyl, ethyl, propyl, isopropyl, butyl sec- and tert-butyl, pentyl, hexyl, heptyl, cyclopropyl, cyclobutyl, cyclopentyl, cyclohexyl, cycloheptyl, norbornyl and the like.

As used herein, the term alkyl includes lower alkyl and extends to cover carbon fragments having up to 20 carbon atoms in straight, branched or cyclic structures. Examples of alkyl groups include octyl, nonyl, undecyl, dodecyl, tridecyl, tetradecyl, pentadecyl, eicosyl, 3,7-ethyl-2,2-methyl4-propylnonyl, cyclododecyl, adamantyl and the like. The terms "lower alkyl" and "alkyl" also include groups having both straight chain and cyclic structures or both branched chain and cyclic structures.

As used herein, the term aryl includes the carbon containing aromatic structures such as phenyl, naphthyl, anthracentyl, phenanthrenyl, pyrenyl, phenyl substituted with one or more alkyls, naphthyl substituted with one or more alkyls, anthracenyl substituted with one or more alkyls, phenanthrenyl substituted with one as more alkyls, and the like.

As used herein, the term halogen includes F, Cl, Br and I.

As used herein, the term "lower alkenyl" includes those alkenyl groups of from 2 to 7 carbon atoms of either a straight, branched or cyclic configuration. Examples of lower alkenyl groups include vinyl, allyl, isopropenyl, pentenyl, hexenyl, heptenyl, cyclopropenyl, cyclobutenyl, cyclopentenyl, cyclohexenyl, cycloheptenyl, 1-propenyl, 2-butenyl, 2-methyl-2-butenyl, norbornenyl and the like.

As used herein, the term "lower alkoxy" includes those alkoxy groups of from 1 to 7 carbon atoms of either a straight, branched or cyclic configuration. Examples of lower alkoxy groups include methoxy, ethoxy, propoxy, isopropoxy, butoxy sec- and tert-butoxy, pentyloxy, hexyloxy, heptyloxy, cyclopropyloxy, cylobutyloxy, cyclopentyloxy, cyclohexyloxy, cycloheptyloxy, norbornyloxy and the like.

As used herein, the term "alkoxy" includes "lower alkoxy" and extends to cover groups having up to 20 carbon atoms in straight, branched or cyclic configurations. Examples of alkoxy groups include octyloxy, nonyloxy, undecyloxy, dodecyloxy, tridecyloxy, tetradecyloxy, pentadecyloxy, eicosyloxy, 3,7-ethyl-2,2-methyl-4-propylnonyloxy, cyclododecyloxy, adamantyloxy and the like.

As used herein, the term "acyl" refers to the carbonyl radical of a carboxylic acid. It will usually be further specified as "alkylacyl"

$$(\text{alkyl-C}(=O)-), \text{"lower alkylacyl" (lower alkyl-C}(=O)-),$$

"arylacyl" $(\text{aryl-C}(=O)-)$, etc., wherein the terms alkyl, lower alkyl and aryl have the meaning given above.

The term essential amino acid is employed to include the following amino acids; alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine.

In those instances when asymmetric centers are present, more than one stereoisomer is possible, and all possible isomeric forms are deemed to be included within the planar structural representations shown. Optically active (R) and (S) isomers may be resolved using conventional techniques known to the skilled artisan.

A preferred embodiment of the present invention relates to compound of the formula I wherein:
each R, each $R^4$, $R^6$, $R^9$, each $R^{10}$, each $R^{13}$, each X, Y¹, Y², Z, each a, each b, each q, each r, t and each Het is as defined above for formula I;

R¹ is H or lower alkyl;

R² is H;

each R³ is independently lower alkyl, lower alkenyl;

each R⁵ is independently H; OR²; or both R⁴'s may be combined to create a doubly bonded oxygen (=O);

each R⁷ is independently COOR⁴; CHO; CH₂OH; tetrazole; or Het;

X¹, X² and X³ are each independently O, S, SO or SO₂;

each n is independently 1 or 2; and each p is O; or the pharmaceutically acceptable salts thereof.

A more preferred embodiment of the present invention relates to compounds of the formula I wherein:

each R is independently H; OH; lower alkyl; trifluoromethyl; lower alkoxy; halogen; N(R⁴)₂; —(C=O)R¹; CH₂OR⁴; CN; SR¹⁰; SOR¹⁰; or SO₂R¹⁰;

R¹ is lower alkyl;

each n is 1; q=O and each of the other substituents is as defined for the aforementioned preferred embodiment, or the pharmaceutically acceptable salts thereof.

A still more preferred embodiment of the present invention are compounds of the formula II:

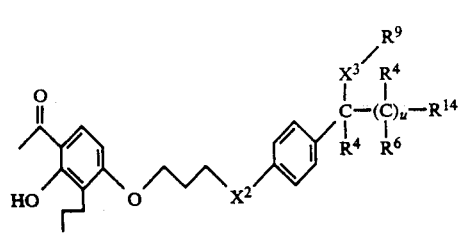
(II)

wherein R⁹ is (CH₂)ₐ—Het, where Het is

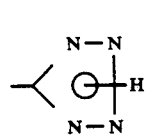 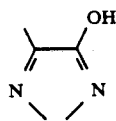 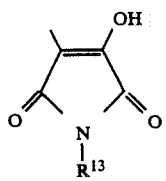

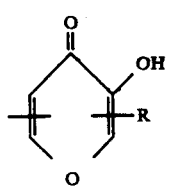 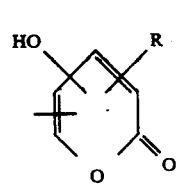 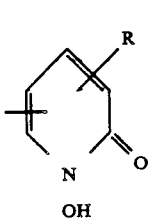

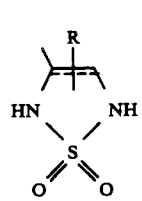 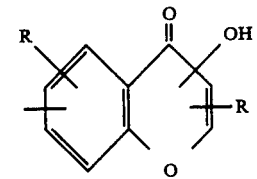

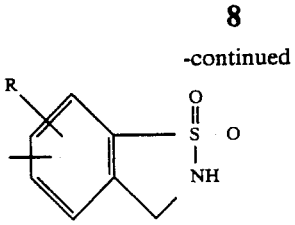 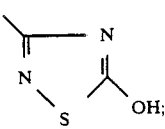

wherein the broken line represents an optional double bond,

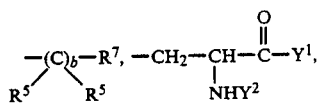

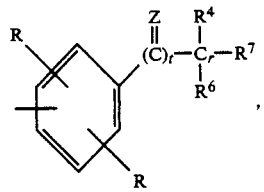

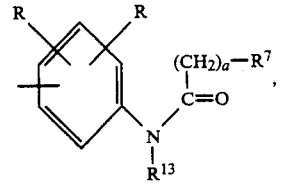

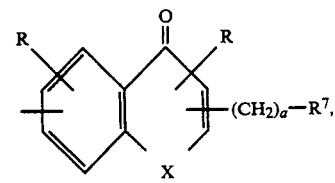

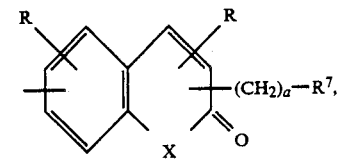

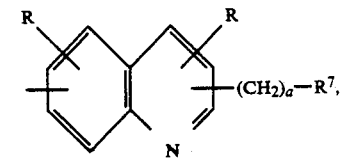

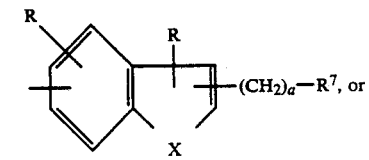

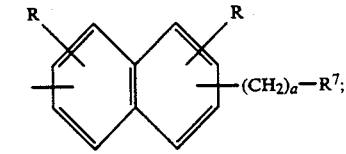

$R^{14}$ is $COOR^4$, u is 0 to 4, and each of the other substituents is as defined for the aforementioned more preferred embodiment,
or the pharmaceutically acceptable salts thereof.

Preferred definitions of Het for compounds of Formula II are:

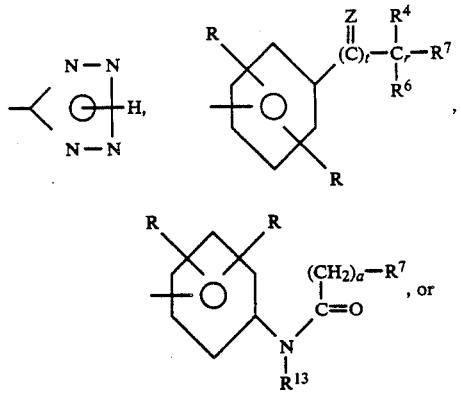

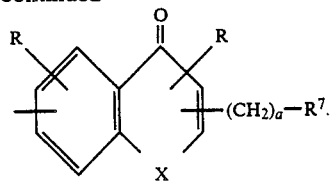

The compounds of the present invention may be prepared by several different routes. According to one method, a hydroxy acid salt of formula X, as described in EP 104,885 (Apr. 4, 1984), converted to the free acid form by acidification and extraction into an organic solvent such as ethyl acetate or ether, and then treated with excess diazomethane to form the ester of formula XI. The ester (XI) is treated with a thiol in 1,2-dichloroethane, or similar inert solvent, in the presence of zinc iodide, or similar Lewis acid catalysts, to form the sulfides of formula XII. Hydrolysis with aqueous base provides the diacids of formula XIII. Hydrolysis to the diacids of formula XIII will cause a conversion to a carboxylic acid or a hydroxycarboxylic acid if $SR^9$ of formula XII contains an ester or a lactone ring. This synthetic route is illustrated below:

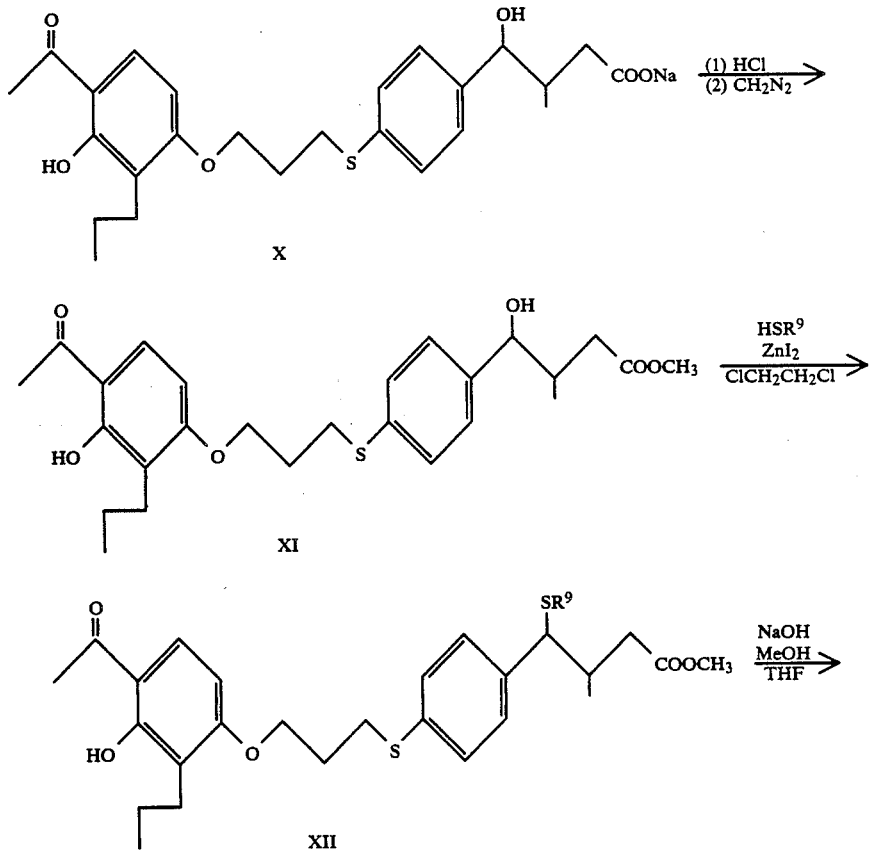

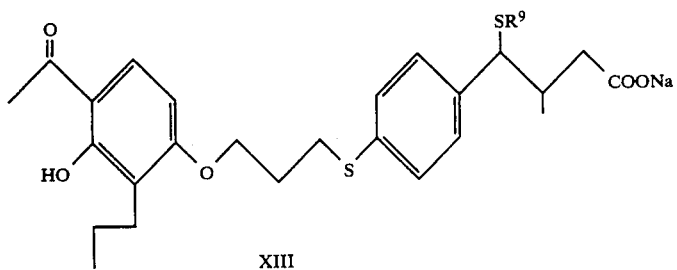

XIII

An alternative procedure is provided whereby the ester of formula XI is reacted with thiolacetic acid and zinc iodide (or similar Lewis acid catalysts) in dichloroethane or a similar inert solvent to provide the thiolacetate of formula XV. Reaction of XV with sodium methoxide in methanol followed by acidification gives the ester of formula XVI. Reaction of XVI with a strong base such as sodium hydride in an inert solvent such as THF at low temperature provides the thiolactones (XVIIa, b) which are separated by chromatography on silica gel or the like. Treatment of one isomeric thiolactone, for example XVIIb, with sodium methoxide followed by reaction of the thiolate anion with a reactive ω-halo-alkanoic acid ester or an alpha, beta-unsaturated alkenoic acid ester, provides the adduct XII which is converted to the diacid salts (XIII) by aqueous alcoholic hydrolysis. Alternatively, the lactone (e.g. XVIIb) can be oxidized with m-chloroperbenzoic acid (mCPBA), or other peracids, or hydrogen peroxide, to provide the sulfones of formula XVIII. Treatment of XVIII, as shown above for XVIIb, provides the diacid salts of formula XX. This procedure is illustrated below:

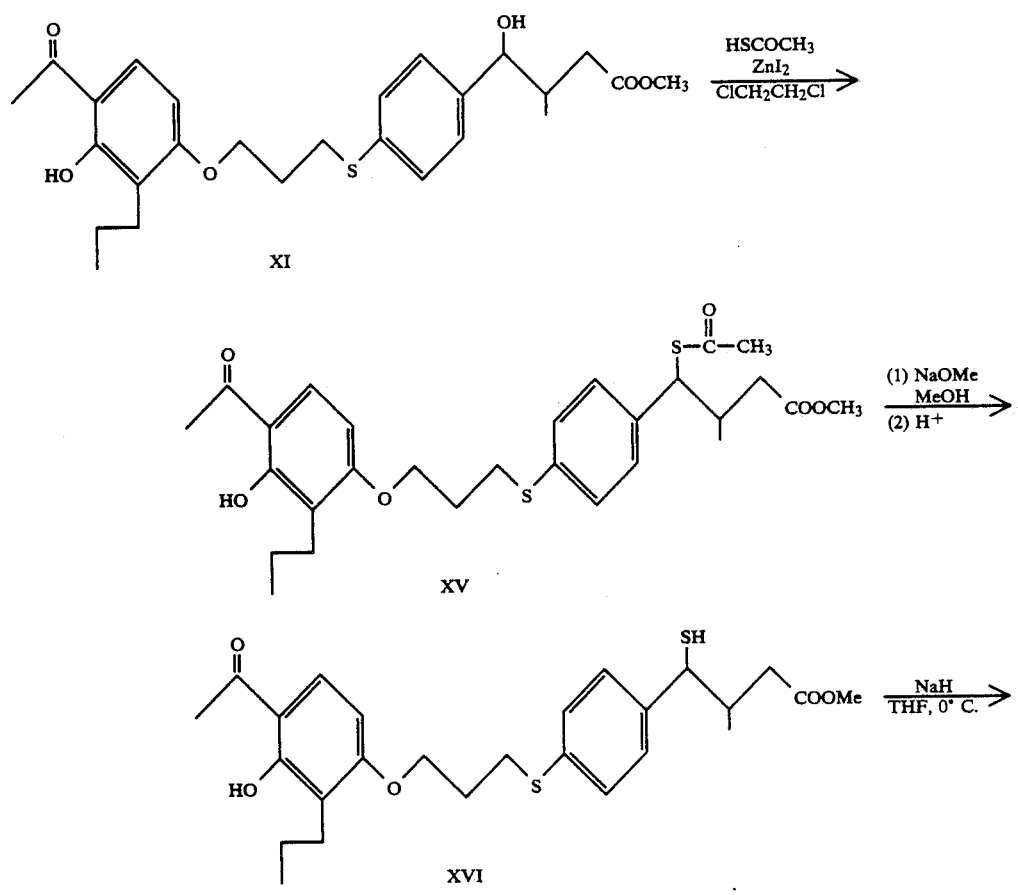

-continued
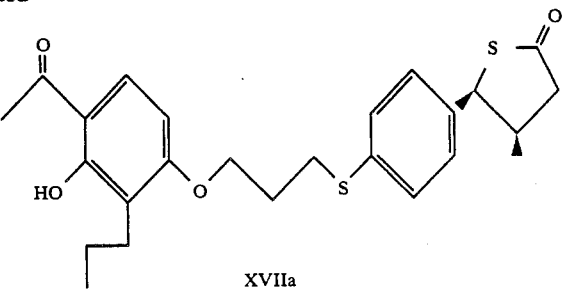
XVIIa
+
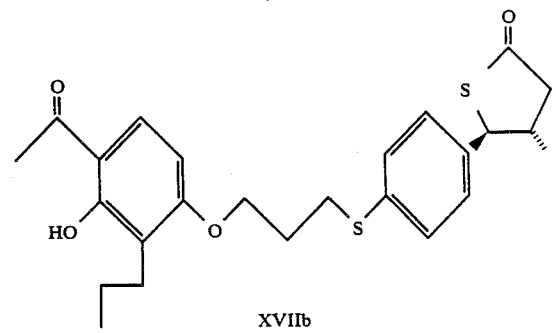
XVIIb
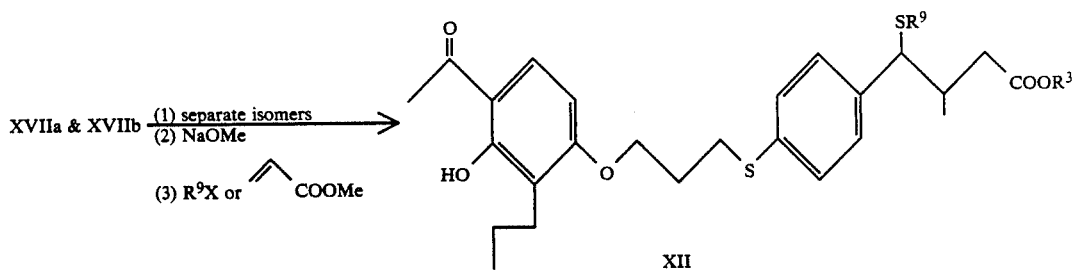
XII
where X is a good leaving group, such as Br, I, etc.
XII $\xrightarrow{\text{hydrolysis}}$ XIII
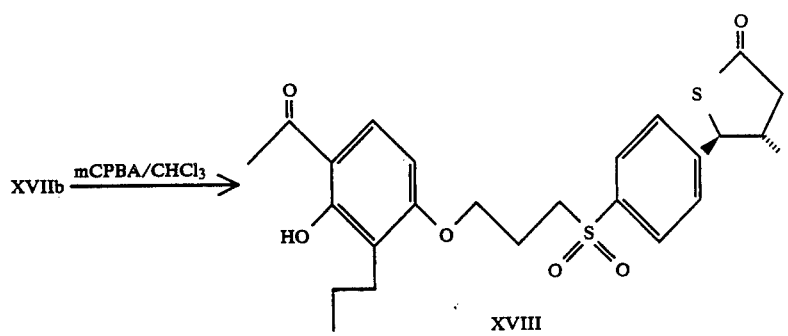
XVIII
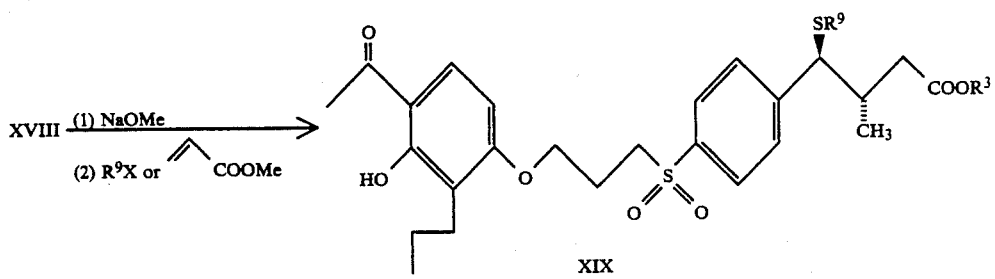
XIX

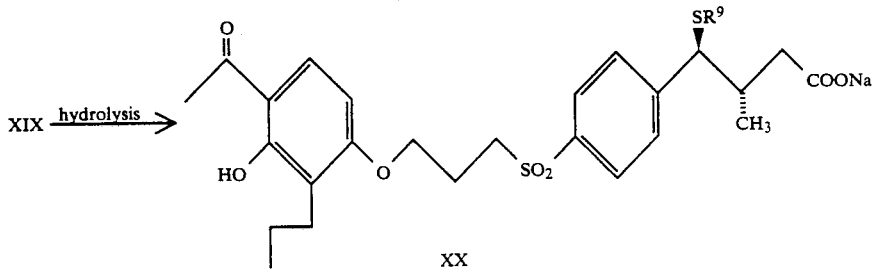

The compounds of Formula I are active as antogonists of SRS-A and the leukotrienes C4, D4 and E4. These compounds also have modest inhibitory activity on leukotriene biosynthesis but are primarily of therapeutic interest as antagonists. The activity of the compounds of Formula I can be detected and evaluated by methods known in the art. See for example, Kadin, U.S. Pat. No. 4,296,129.

The ability of the compounds of Formula I to antagonize the effects of the leukotrienes makes them useful for inhibiting the symptoms induced by the leukotrienes in a human subject. The compounds are valuable therefore in the prevention and treatment of such disease states in which the leukotrienes are the causative factor, e.g. skin disorders, allergic rhinitis, and obstructive airway diseases. The compounds are particularly valuable in the prevention and treatment of allergic bronchial asthma. It will be understood that in this paragraph and in the discussion of methods of treatment which follows, references to the compounds of Formula I are meant to include the pharmaceutically acceptable salts and lactone forms.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanolinduced lesion assay and (B) an indomethacin-induced ulcer assay.

A. Ethanol-Induced Gastric Ulcer Assay

Twenty-four hour fasted Sprague-Dawley (S.D.) rats are perorally (p.o.) dosed with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosae are examined for resulting lesions.

B. Indomethacin-Induced Ulcer Assay

Indomethacin, 10 mg/kg p.o., is used to induce ulcers in 24 hour fasted S.D. rats. Fifteen minutes prior to indomethacin administration, groups of rats each receive either an aqueous vehicle (5% by weight methylcellulose) or the test compound at various doses perorally. Four hours later the animals are sacrificed and stomach mucosae are examined for resulting ulcers.

The magnitude of a prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, antiallergic or anti-inflammatory use and generally, uses other than cytoprotection, lie within the range of from about 0.1 mg to about 40 mg per kg body weight of a mammal, preferably 0.2 mg to about 20 mg per kg, and most preferably 1 to 10 mg per kg, in single or divided doses. On the other hand, it may be necessary to use dosages outside these limits in some cases.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal antiinflammatory drug (NSAID) that might otherwise cause such damage (for example, indomethacin). For such use, the compound of Formula I is administered from 30 minutes prior up to 30 minutes after administration of the NSAID. Preferably, it is administered prior to or simultaneously with the NSAID (for example, in a combination dosage form).

The effective daily dosage level for compounds of Formula I inducing cytoprotection in mammals, especially humans, will generally range from about 0.02 mg/kg to about 100 mg/kg, preferably from about 0.2 mg/kg to about 20 mg/kg. The dosage may be administered in single or divided individual doses.

Any suitable route of administration may be employed for providing a mammal, especially a human with an effective dosage of a leukotriene antagonist. For example, oral, rectal, transdermal, parenteral, intramuscular, intravenous and the like may be employed. Dosage forms include tablets, troches, dispersions, suspensions, solutions, capsules and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, N-ethyl morpholine, N-ethyl piperadine, hydrabamine, morpholine, procaine, 2-dimethylaminoethanol, 2-diethylaminoethanol, tromethamine, lysine, arginine, N,N'-dibenzylethylenediamine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, panoic, pantothenic, phosphoric, succinic, sulfuric, tataric, p-tolnenesulfonic and the like. Particularly preferred are citric, hydrobromic, hydrochloric, maleic, phosphoric, sulfuric and tartaric acids.

The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use is from about 0.1 mg to about 20 mg (preferably from about 0.1 mg to about 10 mg) of a compound of formula I per kg of body weight per day and for cytoprotective use from about 0.02 mg to about 40 mg (preferably from about 0.2 mg to about 20 mg and more preferably from about 1 mg to about 10 mg) of a compound of Formula per kg of body weight per day. In the case where an oral composition is employed, a suitable dosage range for anti-asthmatic, anti-inflammatory or anti-allergic use is, e.g. from about 1 mg to about 40 mg of a compound of formula I per kg of body weight per day, preferably from about 5 mg to about 20 mg per kg and for cytoprotective use from about 0.2 mg to about 40 mg (preferably from about 0.2 mg to about 20 mg and more preferably from about 0.2 mg to about 10 mg) of a compound of Formula I per kg of body weight per day.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosure of which is hereby incorporated herein by reference.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 mg to about 500 mg of the active ingredient.

The following are examples of representative pharmaceutical dosage forms for the compounds of Formula I:

| Injectable Suspension | mg/ml |
|---|---|
| Compound of Formula I | 2.0 |
| Methylcellulose | 5.0 |
| Tween 80 | 0.5 |
| Benzyl alcohol | 9.0 |
| Methyl paraben | 1.8 |
| Propyl paraben | 0.2 |

-continued

| Water for injection to a total volume of 1 ml | |
|---|---|
| Tablet | mg/tablet |
| Compound of Formula I | 25.0 |
| Microcrystalline Cellulose | 325.0 |
| Providone | 14.0 |
| Microcrystalline Cellulose | 90.0 |
| Pregelatinized Starch | 43.5 |
| Magnesium Stearate | 2–2.5 |
| | 500 |
| Capsule | mg/capsule |
| Compound of Formula I | 25.0 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I or XII to the NSAID will generally range from about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

NSAIDs which are within the scope of this invention are those disclosed in EP 140,684 (May 8, 1985) which is hereby incorporated by reference.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985) which are incorporated herein by reference.

The compounds of the Formula I may also be used in combination with leukotriene antagonists such as those disclosed in EP 106,565 (Apr. 25, 1984) and EP 104,885 (Apr. 4, 1984) which are incorporated herein by reference and others known in the art such as those disclosed in European Patent Application Nos. 56,172 and 61,800; and in U.K. Patent Specification No. 2,058,785, which are incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application 11,067 (May 28, 1980) or thromboxane antagonists such as those disclosed in U.S. Pat. No. 4,237,160. They may also contain histidine decarboxyase inhibitors such as α-fluoromethylhistidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles disclosed in EP 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The following examples are provided to aid in the interpretation of the present invention. They are not intended to limit the scope of the invention in any manner. Infrared (IR) spectra were measured as KBr disks or as thin films and absorption bands are reported in reciprocal centimeters ($cm^{-1}$). Nuclear magnetic resonance (NMR) spectra (90 MHz) were measured in deuterochloroform ($CDCl_3$), perdeuterodimethyl sulfoxide (DMSO-$d_6$), perdeuteromethanol ($CD_3OD$), deuterium oxide ($D_2O$) or deuterated trifluoroacetic acid ($CF_3COOD$) and peak positions are expressed in parts per million (ppm) downfield from an internal reference, tetramethylsilane. The following abbreviations are used for peak shapes: s, singlet; d, doublet; t, triplet; q, quartet; and m, multiplet. All melting and boiling Points are reported in degrees Centigrade (° C.) and are uncorrected. Standard abbreviations are used for chemical compounds. For example: THF, tetrahydrofuran; MeOH, methanol; DMF, dimethylformamide; $Et_2O$, di-ethyl ether; and EtOAc, ethyl acetate.

In the following Examples, R* and S* represent a racemic mixture of RS:SR in the ratio of 1:1.

EXAMPLE 1

Preparation of αR*, βR* and αR*, βS* 7-((α-(4-((3-(4-acetyl-3-hydroxy-2-propylphenoxy)-propyl)thio) phenyl)-γ-carboxy-β-methylpropyl)thio)-4-oxo-4-H-1-benzopyran-2-carboxylate disodium salt mixture of diastereomers Step A: Preparation of Methyl 4-((3-(4-acetyl-3-hydroxy-2-propylphenoxy)propyl)thio)-beta-methyl-gamma-hydroxybenzenebutanoate To the 4-((3-(4-acetyl-3-hydroxy-2-propylphenoxy) propyl)thio)-beta-methyl-gamma-hydroxybenzene butanoic acid γlactone (8.84 g, 20 mM) described in EP 104,885 (Apr. 4, 1984) was added a mixture of 2N NaOH (12 ml, 24 mM), THF (50 ml) and MeOH (20 ml) and the mixture was stirred 12 hours under $N_2$. The reaction mixture was evaporated to dryness and dissolved in water (75 ml) and cooled to 0° C.; 1N HCl was added drop wise until the PH was lower than 6 and the organic compound was extracted into EtOAc (200 ml). The organic layer was washed with brine (100 ml) and dried with $Na_2SO_4$. The solvent was removed in vacuo with no heating and the residue was dissolved in $Et_2O$ (100 ml) and cooled to 0° C. Diazomethane (in $Et_2O$) was added in excess and the reaction mixture was evaporated to dryness with no heat and dried under high vacuum to yield the title compound as an oil slightly contaminated (by less than 10 percent of the starting lactone).

$^1$H-250-MHz-NMR/$CDCl_3$:

| Delta (ppm) | Number | m |
|---|---|---|
| 12.7 | 1H | s |
| 7.6 | 1H | d |
| 7.35 | 2H | d |
| 7.25 | 2H | d |
| 6.42 | 1H | d |
| 4.6 | 1H | d |
| 4.15 | 2H | t |
| 3.68 | 3H | s |
| 3.1 | 2H | t |
| 2.8–2.95 | 1H | bs |
| 2.65 | 2H | t |
| 2.55 | 3H | s |
| 2.5–2 | 5H | m |
| 1.55 | 2H | m |
| 0.85–1 | 6H | m |

Step B: Preparation of methyl 7-((1-(4-((3-(4-acetyl-3-hydroxy-2-propylphenoxy)-propyl)thio)phenyl)-3-methoxycarbonyl)-2-methyl-propyl)thio)-4-oxo-4H-1-benzopyran-2-carboxylate To a solution of the ester obtained in Step A (950 mg, 2 mM) of this Example in dry dichloroethane (5 ml) was added dry ZnI₂ (20 mM, 6.4 g) and the Methyl 7-mercapto-4-oxo-4H-1-benzopyran-2carboxylate described in EP 123, 543 (Apr. 19, 1984) (566 mg) and the suspension was efficiently stirred for 3 hours. To the reaction was added IN HCl (20 ml) and methylenedichloride (25 ml). The organic layer was washed with brine (15 ml) and dried with Na₂SO₄. Solvents were removed in vacuo and the residue purified by flash chromatography on silica gel (1:1, hexane:ethyl acetate) and by passing over basic alumina (activity 1) with CH₂Cl₂. Removal of the solvent yielded the title compound as an oil.
¹H-250-MHz-NMR:

| Delta (ppm) | Number | m |
|---|---|---|
| 12.7 | 1H | s |
| 7.85–8 | 1H | dd |
| 7.55 | 1H | d |
| 7.4 | 1H | d |
| 7.0–7.35 | 6H | m |
| 6.4 | 1H | d |
| 4.5 | 1H | t |
| 4.15 | 2H | t |
| 4 | 3H | s |
| 3.6 | 3H | d |
| 3.1 | 2H | t |
| 2.6 | 7H | m |
| 2–2.4 | 3H | m |
| 1.5 | 2H | m |
| 1 and 1.1 | 3H | 2d |
| 0.9 | 3H | t |

Step C: Preparation of αR*, βR* and αR*, 62 S* 7-((α-(4-((3-(4-acetyl-3-hydroxy-2-propylphenoxy)propyl)thio)phenyl)-γ-carboxy-β-methylpropyl)thio)-4-oxo-4-H-1-benzopyran-2-carboxylic acid disodium salt mixture of diastereomers To a solution of the diester obtained in Step B of this Example (188 mg), MeOH (2 ml), and H₂O (2 ml) was added 1M Na₂CO₃ (2 ml) and the mixture was stirred for 96 hours at room temperature. The mixture was then cooled to 0° C. and 1M NaOH (235 §1) was added. The reaction was then stirred for another 48 hours at 5° C. The reaction mixture was evaporated to dryness and absorbed on XAD-8 neutral resin in water, washed with water and then eluted off with ethanol. Evaporation of the solvent in vacuo yielded the title compound.
1H-250 MHz-NMR/DMSO-d₆:

| Delta (ppm) | Number | m |
|---|---|---|
| 12.9 | 1 | broad s |
| 6.6–7.9 | 10 | m |
| 4.8–4.9 | 1 | t |
| 4.1–4.3 | 2 | t |
| 3.1 | 2 | t |
| 0.8–2.9 | 18 | m |

EXAMPLE 2

Preparation of d,l 4-((1-(4-((3-(4-acetyl-3-hydroxy-2-Propylphenoxy)-propyl)thio)phenyl)-3-carboxypropyl) thio)-gamma-oxobenzenebutanoic acid Step A: Preparation of Methyl 4(3-bromopropylthio)gamma-hydroxy-benzenebutanoate To methyl 4(3-bromopropylthio)-gamma-oxobenzene butanoate (described in EP 104,885 (Apr. 4, 1984)) (17.26 g, 50 mM) in 1,2-dimethoxy ethane (100 ml) and MeOH (100 ml) cooled to 0° C., was added CeCl₃ (10 mg) and NaBH₄ (945 mg) portion-wise, over ½ hours and the reaction mixture was maintained at 0° for an additional ½ hour. Thereafter, NaBH₄ (300 mg) was added and reaction stirred for another ½ hour at 0° C. The reaction was slowly poured on cold 1N HCl (200 ml) and extracted with ethyl acetate (300 ml). The organic layer was then washed with brine, dried with Na₂SO₄ and solvents were removed in vacuo at less than 30° C. to yield the title compound as an oil which as used immediately in Step D.

Step B: Preparation of Methyl 4-(methylthio)-gamma-oxo-benzenebutanoate

Thioanisole (12.4 g) and 1,4-dioxo-4-methoxybutyl chloride (16.5 g) in dichloroethane (100 ml) were cooled to 0° C. and aluminum chloride (16 g) was added, followed by another equivalent (16 g) and the reaction mixture was stirred at 0° C. for 2 hours. Ice was added, followed by 1N HCl. Dichloromethane (100 ml) was then added and the organic layer was separated, washed with water and then brine and dried with Na₂SO₄. Removal of the solvents yielded the title compound as an oil.
Analysis calculate: C, 60.48; H, 5.92; S, 13.45.
Found: C, 60.50; H, 5.99; S, 13.27.

Step C: Preparation of Methyl (4-mercapto)-gamma-oxo-benzenebutanoate

To a solution of Methyl (4 methylthio)-gamma- keto-benzene-butanoate (476 mg) in chloroform (15 ml), cooled to 0° C., was added m-chloroperoxybenzoic acid (345 mg) and the mixture was stirred at 0° C. for 1 hour. Excess Ca(OH)₂ was added. The mixture was stirred 0.5 hours at room temperature. Thereafter, filtration through Celite and removal of the solvent left an oily residue of the sulfoxide. Trifluoroacetic anhydride (20 ml) was then added and the mixture was warmed to 40° C. for 15 minutes. Removal of the volatiles left a residue to which was added 50 ml of a 1:1 mixture of MeOH and triethylamine. Solvents were removed in vacuo and further methanol-triethylamine was added and this process was repeated two times. Ethyl acetate (25 ml) was added to the resulting residue. The solution was washed with 1N HCl (10 ml) and then with brine (20 ml) and the organic layer was dried with Na$_2$SO$_4$. Removal of the solvents yielded the title compound which was immediately used in the coupling reaction described in the following step (to avoid formation of the disulfide).

Step D: Preparation of methyl 4((1-(4-(3-bromopropylthio) phenyl)-3-(methoxy carbonyl) propyl)thio)-gamma-oxo-benzenebutanoate To a well stirred suspension of the alcohol obtained in Step A of this Example (694 mg) and ZnI$_2$ (6.4 g) in dichloroethane (10 ml), was added the thiol obtained in Step C of this Example (448 mg) and the mixture was stirred for 3 hours. It was then quenched with 1N HCl (10 ml) and diluted with CH$_2$Cl$_2$ (20 ml). The organic layer was then washed with 1N HCl (10 ml) and then with brine (10 ml) and dried with Na$_2$SO$_4$. Removal of the solvent yielded an oily residue which was purified by flash chromatography (toluene:ethylacetate, 10:1) to yield the pure title compound.

$^1$H-250-MHz-NMR/CDCl$_3$:

| Delta (ppm) | Number | m |
| --- | --- | --- |
| 7.9 | 2H | d |
| 7.3 | 2H | d |
| 7.25 | 4H | s |
| 4.4 | 1H | m |
| 3.75 | 3H | s |
| 3.7 | 3H | s |
| 3.52 | 2H | t |
| 3.25 | 2H | t |
| 3.1 | 2H | t |
| 2.75 | 2H | t |
| 2–2.7 | 6H | m |

Step E: Preparation of methyl 4-((1-(4-(3-(4-acetyl-3-hydroxy-2-propylphenoxy)propyl) thio)phenyl)-3-(methoxycarbonyl)propyl) thio)-gamma-oxo-benzenebutanoate A suspension of the bromide obtained in Step D of this Example (553 mg), 2,4-dihydroxy-3-propyl acetophenone (235 mg), potassium carbonate (400 mg, milled) and methyl ethyl ketone (20 ml) was refluxed for 6 hours. The reaction mixture was then cooled to room temperature and the insolubles removed by filtration through Celite. Solvents were removed in vacuo and the residue was purified on Prep-500 Waters apparatus using toluene: ethyl acetate, 10:1, to yield the title compound.

$^1$H-250 MHz-NMR:

| Delta (ppm) | Number | m |
| --- | --- | --- |
| 12.75 | 1H | s |
| 7.80 | 2H | d |
| 7.55 | 1H | d |
| 7.35 | 2H | d |
| 7.2–7.3 | 4H | m |
| 6.4 | 1H | d |
| 4.4 | 1H | m |
| 4.15 | 2H | t |
| 3.6–3.7 | 6H | 2s |
| 3.25 | 2H | t |
| 3.15 | 2H | t |
| 2.7–2.8 | 2H | t |
| 2.6–2.7 | 2H | t |
| 2.58 | 3H | s |
| 2–2.45 | 6H | m |
| 1.45–1.55 | 2H | m |
| 0.95 | 3H | t |

Step F: Preparation of 4-((1-(4-((3-(4-acetyl-3-hydroxy-2-propylphenoxy)-propyl)thio)phenyl)-3-carboxypropyl)thio)-gamma-oxo-benzenebutanoic acid A solution of the diester obtained in Step E of this Example (922 mg), 1N NaOH (4.2 ml), MeOH (4 ml) and THF (4 ml) was stirred, under N$_2$, for 4 hours, at room temperature. The reaction mixture was then evaporated to dryness and the residue mixed with water (20 ml), acidified with 1N HCL and extracted with diethyl ether (50 ml). The organic layer was washed with brine and dried with Na$_2$SO$_4$. The solvent was removed in vacuo to yield the title compound as a white solid which was purified by trituration with ethyl acetate hexane, 1:5.

Analysis calculated: C, 63.93; H, 6.00; S, 10.04.
Found: C, 64.10; H, 5.99; S, 9.73.

EXAMPLE 3

Preparation of $\beta R^*$, $\gamma R^*$ and $\beta S^*$, $\gamma R^*$ 4-((3-(4-acetyl-3-hydroxy-2-propylphenoxy)propyl)thio)-gamma-(3-((carboxyacetyl)amino)phenyl)thio-Beta-methylbenzenebutanoic acid Step A: Preparation of ethyl 3-oxo-3-(3-mercaptophenylamino) propanoate A mixture of 3-aminothiophenol (5.0 g) and diethyl malonate (6.41 g) was heated under a nitrogen atmosphere for 2 hours at from 165° to 170° C. The mixture was chromatographed on silica gel to yield the title compound, m.p. 52°–54°.

Analysis calculated: C, 55.21; H, 5.47; N, 5.85; S, 13.39.
Found: C, 54.64; H, 5.41; N, 5.80; S, 13.02.

Step B: Preparation of Methyl 4-((3-(4-acetyl-3-hydroxy-2-propylphenoxy)propyl)thio)-gamma-((3-ethoxy-1,3-dioxopropylamino)phenyl)-thio)beta-methylbenzenebutanoate To a well stirred suspension of the alcohol obtained in Step A, Example 1 (1.422 g) and ZnI$_2$ (6 g) in dichloroethane (25 ml) was added the thiol obtained in step A, Example 3 (550 mg) and the mixture was stirred for 3 hours. Thereafter, 1N HCl (20 ml) was added, followed by dichloromethane (50 ml). The organic layer was separated, washed with brine and then dried with Na$_2$SO$_4$. The solvents were removed in vacuo to give a residue which was purified by flash chromatography using 33% ethyl acetate in hexane to yield the title compound as an oil (1.76 g, 84%).

$^1$H-250 MHz-NMR/CDCl$_3$:

| Delta (ppm) | Number | m |
| --- | --- | --- |
| 12.75 | 1H | s |
| 9.2 | 1H | bs |
| 7.5 | 1H | d |
| 7.52 | 1H | s |

| Delta (ppm) | Number | m |
|---|---|---|
| 6.8–7.4 | 7H | m |
| 6.4 | 1H | d |
| 4.2–4.35 | 3H | m |
| 4.15 | 2H | t |
| 3.65 | 3H | 2s |
| 3.45 | 2H | s |
| 3.1 | 2H | t |
| 2–2.85 | 10H | m |
| 1.55 | 2H | m |
| 1.3 | 3H | t |
| 0.9–1.15 | 6H | m |

Step C: Preparation of 4-((3-(4-acetyl-3-hydroxy-2-propylphenoxy)propyl)thio)-gamma-((3-carboxyacetate)amino)phenyl)thio)beta-methylbenzenebutanoic acid To a cooled (0° C.) solution of the ester obtained in Step B of this Example (615 mg), MeOH (5 ml) and THF (5 ml) was added 1N NaOH (2.6 ml) and the reaction mixture was allowed to return to room temperature and was stirred for 12 hours. Thereafter, the solvents were removed in vacuo and the residue was diluted with water (10 ml), acidified with 1N HCL (5 ml) and extracted with ether (30 ml). The organic layer was washed with brine, dried with $Na_2SO_4$ and evaporated to dryness in vacuo to yield the title compound as a beige foam (520 mg, 90%).

Analysis calculated: C, 62.46; H, 6.01; N, 2.14; S, 9.81.
Found C, 62.00; H, 6.24; N, 2.07; S, 9.98.

EXAMPLE 4

Preparation of 1R*, γR* and 1R*, γS* 4-((1-(4((3-(4-acetyl-3-hydroxy-2-propylphenoxy)-propyl)thio)phenyl)-3-carboxypropyl)thio)-beta-methyl-gammaoxobenzenebutanoic acid (mixture of diastereoisomers)

Step A: Preparation of Methyl (1((4(3-bromopropylphenyl)-3-methoxycarbonylpropyl)thio)-β-methyl-gamma-oxobenzene-butanoate To a solution of the alcohol obtained in Step A of Example 2 (1.041 g), $ZnI_2$ (9.6 g) and dichloroethane (15 ml), was added methyl 4-mercaptobeta-methyl-gamma-oxobenzenebutanoate from Example 9, Step E (714 mg) under efficient stirring and the reaction mixture was stirred for 3 hours. The reaction mixture was then quenched with water (10 ml) and then diluted with $CH_2Cl_2$ (25 ml). The organic layer was then washed with 1 N HCl (25 ml) and then with brine and was then dried with $Na_2SO_4$. Removal of the solvents in vacuo yielded a residue which was purified by flash chromatography (10:1, toluene:ethylacetate) to yield the title compound as an oil (1.6 g, 94%).

1-250 MHz-NMR/CDCl₃:

| Delta (ppm) | Number | m |
|---|---|---|
| 7.84 | 2H | d |
| 7.29 | 2H | d |
| 7.24 | 4H | s |
| 4.4 | 1H | m |
| 3.86 | 1H | m |
| 3.64 | 6H | 2s |
| 3.51 | 2H | t |
| 3.07 | 2H | t |
| 2.94 | 1H | m |

| Delta (ppm) | Number | m |
|---|---|---|
| 2.05–2.54 | 7H | m |
| 1.19 | 3H | d |

Step B: Preparation of Methyl 4-((1-(4-((3-(4-acetyl-3-hydroxy-2-propylphenoxy)-propyl)thio)phenyl)-3-methoxycarbonylpropyl)thio)-beta-methyl-gammaoxobenzene butanoate A solution made of the bromide obtained in Step A of this Example (1.55 g), 2,4-dihydroxy-3-propyl acetophenone (652 mg), and milled $K_2CO_3$ (1.16 g) in MEK (methyl ethyl ketone) (25 ml) was refluxed for hours and then cooled to room temperature. The mixture was filtered and removal of the solvent left a residue which was purified by flash chromatography with 30% ethyl acetate in hexane to yield the title compound as an oil (1.05 g, 55%).

1-250 MHz-NMR(CDCl₃):

| Delta (ppm) | Number | m |
|---|---|---|
| 12.75 | 1H | s |
| 7.83 | 2H | d |
| 7.6 | 1H | d |
| 7.45 | 2H | d |
| 7.3 | 4H | s |
| 6.42 | 1H | s |
| 4.4 | 1H | m |
| 4.15 | 2H | t |
| 3.85 | 1H | m |
| 3.65 | 6H | 2s |
| 3.12 | 2H | t |
| 2.65 | 2H | AB |
| 2.1–2.7 | 11H | m |
| 1.55 | 2H | m |
| 1.2 | 3H | d |
| 0.95 | 3H | t |

Step C: Preparation of 1R*γR*, 1R*γS* 4-((1-4-((3-(4-acetyl-3-hydroxy-propylphenoxy)propyl)thio)phenyl)-3-carboxypropyl)thio)-beta-methyl-gamma-oxobenzenebutanoic acid (mixture of diastereoisomers)

To a solution of the diester from Step B of this Example (940 mg) in MeOH (4 ml) and THF (4 ml) was added 1N NaOH (4.2 ml) and the reaction mixture was stirred for 3 hours at room temperature. Solvents were removed in vacuo and the residue mixed with water (20 ml) and acidified with 1N HCl (10 ml). The aqueous layer was extracted with ether (50 ml) and the organic layer was washed with brine (10 ml) and then dried with $Na_2SO_4$. The solvents were removed in vacuo to give the title compound as a beige foam (740 mg, 82%).

Analysis calculated: C, 64.40; H, 6.18; S, 9.82
Found: C, 64.34; H, 6.12; S, 9.82.

EXAMPLE 5

Preparation of αR*, βR* and αR*, βS*
N(S(α-(4-((3-(4-acetyl-3-hydroxy-2-propylphenoxy)-propyl)thio)
phenyl)-γ-carboxy-β-methylpropyl)-cysteinyl)glycine
(mixture of diastereoisomers)disodium salt Step A: Preparation of
N(S-(α(4-((3-(4-acetyl-3-hydroxy-2-propylphenoxy)-propyl)thio)phenyl)-γ-methoxycarbonyl-β-methyl-propyl)N-trifluoroacetylcysteinyl)glycine methyl ester
(mixture of diastereoisomers)

To a well stirred suspension of the ester obtained in Step A, Example 1 (474 mg), $ZnI_2$ (3.2 g) and dichloroethane (3 ml) was added cysteinylglycine methyl ester and the mixture was stirred for 3 hours. Thereafter, water (5 ml), 1N HCL (5 ml) and dichloromethane (25 ml) were added. The organic layer was washed with brine and then dried with $Na_2SO_4$. The solvents were removed to yield a residue which was chromatographed to yield the title compound as an oil (436 mg, 59%).

¹-250 MHz/CDCl₃:

| Delta (ppm) | Number of H | m |
|---|---|---|
| 12.9 | 1 | s |
| 7.6 | 1 | d |
| 7.4–7.55 | 1 | m |
| 7.15–7.35 | 4 | m |
| 6.6–6.7 | 1 | m |
| 6.4 | 1 | d |
| 4.7–3.5 | 13 | m |
| 3.1–3.2 | 2 | t |
| 2.9–2 | 11 | m |
| 1.5 | 2 | m |
| 0.8–1.1 | 6 | m |

Step B: Preparation of αR*, βS* and αR*, βR*
N-(S-(α-(4-((3-(4-acetyl-3-hydroxy-2-propylphenoxy)
propyl)thio)phenyl)-γ-carboxy-β-methylpropyl)
cysteinyl)glycine (mixture of diastereoisomers)
disodium salt To a solution made of the ester obtained in Step A of this Example (390 mg), MeOH (3 ml) and THF (3 ml) was added 1N NaOH (2 ml) and the mixture was stirred for 12 hours. Thereafter, solvents were removed and the residue passed on a XAD-8 neutral resin to yield the title compound as a beige foam (275 mg, 80%).

Analysis calculated: C, 51.64; H, 5.63; S, 9.19.
Found C, 51.44; H, 5.97; S, 8.54.

EXAMPLE 6

Preparation of βR*, αR* and βR*, αS*
4-((3-(4-acetyl-3-hydroxy-2-propylphenoxy)propyl)thio)-gamma-((2-carboxyethyl)thio)-beta-methylbenzenebutanoic acid disodium salt (mixture of diastereoisomers)

Step A: Preparation of Methyl
4-((3-(4-acetyl-3-hydroxy-2-propylphenoxy)propyl)thio)-gamma((2-methoxycarbonylethyl)thio)-beta-methylbenzenebutanoate (mixture of diastereoisomers)

To an efficiently stirred suspension made of the alcohol obtained from Step A of Example 1 (1.42 g), $ZnI_2$ (4.8 g) in dichloroethane (20 ml) was added methyl 3-mercaptopropionate (360 mg) and the suspension was stirred for 3 hours. Thereafter, 1N HCl (20 ml) and dichloromethane (50 ml) were added. The organic layer was then washed with brine and dried with $Na_2SO_4$. The solvents were removed in vacuo to yield a residue which was chromatographed on silica gel to yield the title compound as an oil (1.37 g, 80%).

NMR ¹H-250 MHz/CDCl₃:

| Delta (ppm) | Number of H | m |
|---|---|---|
| 12.9 | 1 | s |
| 7.55 | 1 | d |
| 7.2–7.4 | 4 | m |
| 6.45 | 1 | d |
| 4.15 | 2 | t |
| 3.6–3.8 | 1 | m |
| 3.65 | 3 | 2s |
| 3.65 | 3 | s |
| 3.15 | 2 | t |
| 2.8–2.0 | 14 | m |
| 1.55 | 2 | m |
| 0.95 | 6 | m |

Step B: Preparation of βR*, αR* and βR*, αS*
4-((3-(4-Acetyl-3-hydroxy-2-propylphenoxy)propyl)
thio-gamma-((2-carboxyethyl)thio)-betamethylbenzenebutanoic acid disodium salt tetrahydrate (mixture of diastereoisomers)

To a solution made of the ester obtained in Step A of this Example (1.3 g), MeOH (10 ml), and THF (10 ml) was added 1N NaOH (6.7 ml) and the mixture was stirred for 12 hours. Thereafter, the solvents were removed in vacuo. The residue was then mixed with water and passed over XAD-8 neutral resin to yield the title compound as a beige foam (780 mg, 60%).

Analysis calculated: C, 50.59; H, 6.37; S, 9.65; Na, 6.92.
Found: C, 50.40; H, 6.31; S, 9.69; Na, 6.36.

EXAMPLE 7

Preparation of βR*, γR* and βR*, γS*
4-((3-(4-Acetyl-3-hydroxy-2-propylphenoxy)propyl)-thio)-gamma-(butylthio)-beta-methylbenzenebutanoic acid (mixture of diastereoisomers)

Step A: Preparation of Methyl
4-((3-(4-acetyl-3-hydroxy-2-propylphenoxy)propyl)thio)-gamma(thioacetyl)-beta-methylbenzenebutanoate
(mixtures of diastereoisomers)

To a solution of the alcohol obtained in Step A, of Example 1 (5.69 g), $ZnI_2$ (19 g) in dichloroethane (50 ml) was added thioacetic acid (1.005 g) with efficient stirring. After 3 hours, 1N HCl (25 ml), water (25 ml) and dichloromethane (150 ml) were added. The organic layer was washed with brine and dried with $Na_2SO_4$. The solvents were then removed in vacuo to yield a residue which was chromatographed to yield the title compound as an oil (5.43 g, 85%).

Analysis calculated: C, 63.13; H, 6.81; S, 12.04.
Found: C, 63.01; H, 6.77; S, 11.77.
NMR, ¹H-250 MHz/CDCl₃:

| Delta (ppm) | Number of H | m |
|---|---|---|
| 12.9 | 1 | s |
| 7.6 | 1 | d |
| 7.1–7.3 | 4 | m |
| 6.4 | 1 | d |

-continued

| Delta (ppm) | Number of H | m |
|---|---|---|
| 4.5 | 1 | m |
| 4.1 | 2 | t |
| 3.6–3.7 | 3 | 2s |
| 3.15 | 2 | t |
| 2.75–2 | 13 | m |
| 1.5 | 2 | m |
| 0.8–1.1 | 6 | m |

Step B: Preparation of βR, γR* and βR*, γS* Methyl 4-((3-(4-acetyl-3-hydroxy-2-propylphenoxy) propyl)thio)-gamma-(butylthio)-beta-methylbenzenebutanoate (mixture of diastereoisomers)

To a cooled (0° C.) solution of the thioacetate obtained in Step A of this Example (532 mg) in MeOH (5 ml) was added 2N NaOMe (650 microliters) followed, ½ hour later, by 1-iodobutane (148 microliters, 240 mg) and the reaction mixture was stirred for 1 hour at 0° C. 1N HCl (5 ml) was added followed by ethyl acetate (25 ml). The organic layer was collected, washed with brine and dried. Solvents were removed in vacuo and the residue purified by chromatography to yield the title compound as an oil (465 mg, 85%).

| Delta (ppm) | Number of H | m |
|---|---|---|
| 12.9 | 1 | s |
| 7.65 | 1 | d |
| 7.1–7.4 | 4 | m |
| 6.4–6.5 | 1 | d |
| 4.15 | 2 | t |
| 3.5–3.8 | 4 | m |
| 3.1–3.2 | 2 | t |
| 2–2.8 | 12 | m |
| 1.2–1.7 | 6 | m |
| 0.75–1.15 | 9 | m |

Step C: Preparation of βR*, γR* and βR*, γS* 4-((3-(4-Acetyl-3-hydroxy-2-propylphenoxy)propyl) thio)-gamma-(butylthio)-beta-methylbenzenebutanoic acid (mixture of isomers)

To a solution of the ester from Step B of this Example (340 mg) in MeOH (3 ml) and THF (3 ml) was added 1N NaOH (1.6 ml) and the mixture was stirred for 12 hours. Thereafter, the solvents were removed and the residue mixed with water (10 ml), acidified with 1N HCl (5 ml) and extracted with ethyl acetate (25 ml). The organic layer was washed with brine and dried with $Na_2SO_4$. The solvents were removed in vacuo to give a residue which was chromatographed to yield the title compound (210 mg, 63%).

Analysis calculated: C, 65.38; H, 7.57; S, 12.04.
Found: C, 65.25; H, 7.68; S, 12.11.

EXAMPLE 8

Preparation of βR*, γR* and βR*, γS* 4-((3-(4-Acetyl-3-hydroxy-2-propylphenoxy)propyl)-thio)-beta-methyl-gamma-((1H-tetrazol-5-ylmethyl)thio)benzeneanoic acid disodium salt monohydrate and Methyl βR*, γR* and 62 R*, γS* 4-((3-(4-acetyl-3-hydroxy-2-propylphenoxy)propyl)thio)-beta-methylgamma-((1H-tetrazole-5-yl-methyl)thio)-benzenebutanoate (diastereoisomer mixture) sodium salt Step A: Preparation of Methyl βR*, γR* and βR*, γS* 4-((3-(4-acetyl-3-hydroxy-2-propylphenoxy) propyl)thio)-beta-methyl-gamma-(cyanomethyl) thio)benzenebutanoate (mixture of isomers)

To a cooled (0° C.) solution of the acetate obtained in Step A of Example 7 (2.66 g) in MeOH (30 ml) was added 2N NaOMe (3.25 ml) and the reaction mixture was stirred for ½ hour. Thereafter, chloroacetonitrile (491 mg) was added and the mixture stirred for another hour. The mixture was slowly poured on ice cold 1N HCl (100 c.c.). Ethyl acetate (100 ml) was then added and the organic layer was separated. The aqueous layer was extracted with ethyl acetate (50 ml) and the combined organic layers were washed with brine and dried with $Na_2SO_4$. The solvents were removed to yield a residue which was chromatographed to yield the title compound as an oil.

NMR $^1$H-250 MHz/CDCl$_3$:

| Delta (ppm) | Number of H | m |
|---|---|---|
| 12.9 | 1 | s |
| 7.6 | 1 | d |
| 7.15–7.35 | 4 | m |
| 6.45 | 1 | d |
| 4.15 | 2 | t |
| 3.85–4.05 | 1 | m |
| 3.5–3.6 | 3 | 2s |
| 3.1–3.2 | 2 | t |
| 2.9–2.0 | 12 | m |
| 1.45–1.6 | 2 | m |
| 0.85–1.2 | 6 | m |

Step B: Preparation of βR*, γR* and βR*, γS* 4-((3-(4-Acetyl-3-hydroxy-2-propylphenoxy)propyl) thio)-beta-methyl-gamma-((1H-tetrazole-5-ylmethyl)-thio)benzenebutanoic acid sodium salt monohydrate and Methyl βR*, γR* and βR*, γS* 4-((3-(4-acetyl-3-hydroxy-2-propylphenoxy)propyl) thio)-beta-methyl-gamma-((1H-tetrazole-5-ylmethyl)-thio)benzenebutanoate (diastereoisomer mixture) sodium salt The ester obtained in Step A (2.54 g) and tri-n-butyl-tin azide (1.75 g) were heated, neat, under $N_2$, to 80° C. for 16 hours. Ether (100 ml) saturated with HCl gas was added and the mixture was stirred at room temperature for 3 hours. It was then diluted with ether (100 ml) and stirred with (100 ml) 2N NaOH at room temperature for 30 minutes. The aqueous layer was separated and the ether layer was extracted back with 2N NaOH (100 ml). The combined aqueous layers were acidified and extracted with ethyl acetate. The ethyl acetate solution was dried with brine and sodium sulfate (anhydrous).

The solvent was removed to yield an oil which was purified by flash chromatography. This yielded the tetrazole/acid and the tetrazole/ester. Both were converted to their respective sodium salts with sodium hydroxide and purified on XAD-8 neutral resin.

Analysis calculated for $C_{27}H_{29}O_5S_2N_4Na_2 \cdot H_2O$: C, 52.50; H, 5.06; N, 9.07; S, 10.38; Na, 7.44. Found: C, 52.39; H, 5.45; N, 8.72; S, 10.54; Na, 7.03.

Analysis calculated for $C_{28}H_{32}O_5S_2N_4Na \cdot H_2O$: C, 55.16; H, 5.62; S, 10.52. Found: C, 55.18; H, 6.10; S, 10.71.

EXAMPLE 9

Preparation of 1R, 2R, βR, γS; 1R, 2S, βR, γS; 1S; 2R, βR, γS; 1S, 2S, βR, γS; 1R, 2R, βS, γR; 1R, 2S, βS, γR; 1S, 2R, βS, γR; 1S, 2S, βS, γR 4-((1-(4-((3-(4-Acetyl-3-hydroxy-2-propylphenoxy)-propyl)thio)phenyl)-3-carboxy-2-methylpropyl)thio)-gamma-hydroxy-betamethylbenzenebutanoic acid disodium salt monohydrate

Step A: Preparation of 4-(Methylthio)phenyl-propan-1-one

To a solution of thioanisole (5 g) and propionyl chloride (3.9 ml) in dichloroethane (80 ml) at 0° C. was added, in portions, aluminum chloride (6.4 g). The mixture was stirred overnight at room temperature. The reaction mixture was poured onto a mixture of ice and water (200 ml) and concentrated HCl (2 ml) and extracted with $CH_2Cl_2$. The combined organic layers were washed with water, dried over $Na_2SO_4$ and purified on a silica gel column (140 g) using hexane/EtOAc (10:1) as eluant to afford the title compound as a white solid, m.p. 60°–61° C.

Step B: Preparation of Methyl 4-(methylthio)-beta-methyl-gamma-oxobenzenebutanoate To a solution of potassium hexamethylsilazane (0.158 mole) in toluene (254 ml) and THF (160 ml) at −78° C. was added dropwise the ketone from Step A of this Example (25.8 g) in THF (90 ml). The reaction mixture was stirred 30 minutes at −78° C. Methyl bromoacetate (16.2 ml) in THF (25 ml) was added dropwise. After stirring 1.5 hours at −78° C. the reaction mixture was poured into 1N HCl (400 ml). The organic layer was separated and the aqueous layer was further extracted with ethyl acetate. The combined organic layers were washed with water, dried over $Na_2SO_4$ and evaporated to give a yellow oil which was purified on a flash silica gel column (1 kg) using hexane/EtOAc (10:2) as eluant to give the title compound as an oil.

$^1H$ NMR (CDCl$_3$) delta: 1.2 (3H, d, J=6 Hz), 2.45 (3H, s), 2.3–3.1 (2H, m), 3.6 (3H, s), 3.85 (1H, quinteuplet, J=6 Hz), 7.25 (2H, d, J=7 Hz), 7.9 (2H, d, J=7 Hz).

Step C: Preparation of Methyl 4-(methylsulfinyl)beta-methyl-gamma-oxobenzenebutanoate To a solution of the sulfide from Step 2 (14.6 g) in $CH_2Cl_2$ (75 ml) at 0° C. was added dropwise a solution of 85% m-CPBA (11.7 g) in $CH_2Cl_2$ (225 ml). The reaction mixture was stirred for 2 hours at 0° C. and solid calcium hydroxide (6.4 g) was added and stirred at room temperature for 15 minutes and filtered through a bed of Celite. The filtrate was evaporated to give an oil which was purified on a flash silica gel column (175 g) using $CH_2Cl_2$/acetone (10:1) as eluant to afford the title compound as a colorless oil (13.5 g, 87%).

$^1H$ NMR (CDCl$_3$) delta: 1.23 (3H, d, J=6 Hz), 2.45–2.57 and 2.95–3.1 (2H, m), 2.78 (3H, s), 3.65 (3H, s), 3.95 (1H, quintuplet), 7.78 (2H, d, J=7 Hz), 8.15 (2H, d, J=7 Hz).

Step D: Preparation of Methyl 4-(trifluoroacetoxymethylthio)-beta-methyl-gamma-oxobenzenebutanoate A solution of the sulfoxide from Step C of this Example (10 g) in trifluoroacetic anhydride (50 ml) was heated at 45° C. for 25 minutes and the mixture was evaporated, and then coevaporated with toluene, to dryness to give the title compound as an oil (15 g, crude) which was used directly in the following step.

$^1H$ NMR (CDCl$_3$) delta: 1.23 (3H, d, J=6Hz), 1 45–1.52 (1H, dd), 1.93–2.05 (1H, m), 3.65 (3H, s), 3.85–4.0 (1H, m), 5.7 (2H, s), 7.55 (2H, d, J=7 Hz), 7.97 (2H, d, J=7 Hz).

Step E: Preparation of Methyl 4-mercapto-beta-methyl-gamma-oxobenzenebutanoate To the neat trifluoroacetate from Step D of this Example (12.3 g) was added a mixture of 1:1 MeOH-NEt$_3$ (600 ml) and the resulting reaction mixture was evaporated under vacuum. The procedure was repeated twice more. The residue was dissolved in $CH_2Cl_2$, washed with 1N HCl and brine and dried over $Na_2SO_4$. Evaporation of the solvent gave the title compound as an oil (7.8 g, 97%).

$^1H$ NMR (CDCl$_3$) delta: 1.23 (3H, d, J=6 Hz), 2.45–2.52 (1H, dd), 2.93–3.05 (1H, m), 3.65 (3H, s), 3.85–4.0 (1H, m), 7.32 (2H, d, J=7 Hz), 7.85 (2H, d, J=7 hz).

Step F: Preparation of Methyl 4-(S-dimethylthiocarbamoyl)-beta-methyl-gamma-oxobenzenebutanoate To a solution of the thiol from Step E of this Example (7.5 g) in DMF (100 ml) at 0° C. was added in two portions 99% NaH (835 mg) and stirred for 30 minutes at 0° C. To this mixture was added dimethylcarbamoyl chloride (3.8 ml) and stirred for 15 minutes at 0° C. and 30 minutes at room temperature. The reaction mixture was poured onto a mixture of ice and water (300 ml) and extracted with EtOAc. The combined organic layers were washed with brine, dried over $Na_2SO_4$ and evaporated to give a yellow oil which was purified on a flash silica gel column (500 g) using hexane/EtOAc (2:1) as eluant to give the title compound as an oil (7.8 g, 77%).

$^1H$ NMR (CDCl$_3$) delta: 1.23 (3H, d, J=6 Hz), 2.45–2.55 (1H, dd), 2.93–3.05 (1H, m), 3.0–3.2 (6H, d(b)), 3.65 (3H, s), 3.85–4.0 (1H, m), 7.62 (2H, d, J=7 Hz), 7.97 (2H, d, J=7 Hz).

Step G: Preparation of 4-(S-Dimethylthiocarbamoyl)beta-methyl-gamma-oxobenzenebutanoic acid To a solution of the ester from Step F of this Example (7.6 g) in MeOH (110 ml) at 0° C. was added 2N NaOH (37 ml) and the mixture was stirred at 0° C. for 1 hour. The reaction mixture was poured into a mixture of ice and water (300 ml), acidified with concentrated HCl and extracted with EtOAc. The combined organic layers were washed with water, dried over $Na_2SO_4$ and evaporated to give the title compound as an oil (7.3 g, 100%).

$^1$H NMR (CDCl$_3$) delta: 1.23 (d, 3H, J=6 Hz), 2.4–2.55 (1H, dd), 2.85–3.05 (1H, m), 3.0–3.2 (6H, d(b)), 3.8–4.0 (1H, m), 7.6 (2H, d, J=7 Hz), 7.95 (2H, d, J=7 Hz).

Step H: Preparation of βR*, γS* 4-(S-Dimethylthiocarbamoyl) beta-methyl-gamma-hydroxybenzenebutanoic acid gamma-lactone To a solution of the ketone from Step G of this Example (6.85 g) in dry THF (190 ml) at −78° C. was added dropwise, under nitrogen, a solution of 1.5M diisobutyl aluminum hydride (DIBAL-H) in toluene (37 ml) and stirred at −78° C. for 1.5 hours. The reaction mixture was poured into cold 1N HCl (600 ml) and extracted with EtOAc. The combined organic layers were washed with brine, dried over Na$_2$SO$_4$ and evaporated to give an oil which was dissolved in CH$_2$Cl$_2$ (200 ml) and trifluoroacetic acid (70 drops) was added and the mixture stirred at room temperature for 2 hours. The reaction mixture was diluted with toluene and evaporated to give an oil which was purified on flash silica gel column (350 g) using hexane/EtOAc (1:1) as eluant to give the title compound as a white solid (3.4 g, 52%): m.p. 113°–115° C.

$^1$H NMR (CDCl$_3$) delta: 0.73 (cis) and 1.2 (trans) (3H, d, J=7 Hz), 2.27–2.45 (1H, dd), 2.75–3.0 (2H, m), 3.0–3.2 (6H, d(b)), 4.97 (trans) and 5.6 (cis) (1H, d, J=5.6 Hz), 7.27 (2H, d, J=7 Hz), 7.55 (2H, d, J=7 Hz).

Unreacted starting material was recovered from the column by eluting with toluene-dioxaneacetic acid (10:2:0.1) to recover 2.2 g (32%) as an oil.

Step I: Preparation of βR*, γS* 4-mercapto-beta-methyl-gamma-hydroxybenzenebutanoic acid gamma-lactone To a suspension of the thiocarbamate from Step H of this Example (3 g) in MeOH (160 ml) was added 2N NaOH (54 ml) and the mixture refluxed under N$_2$ for 1.5 hours. The reaction mixture was cooled to room temperature, diluted with water (500 ml), acidified with 2N HCl and extracted with ethyl acetate. The combined organic layers were washed with water, dried over Na$_2$SO$_4$ and evaporated to give an oil which was dissolved in CH$_2$Cl$_2$ (100 ml) and treated with trifluoroacetic acid (30 drops) from 3 hours at room temperature. The reaction mixture was evaporated and coevaporated with toluene to give the title compound as an oil 2.39 g).

$^1$H NMR (CDCl$_3$) delta: 0.73 and 1.2 (3H, d, J=7 Hz), 2.27–2.45 (1H, dd), 2.75–2.95 (2H, m), 2.5 (1H, s), 4.9 and 5.55 (1H, d, J=5.6 Hz), 7.1 (2H, d, J=7 Hz), 7.3 (2H, d, J=7 Hz).

Step J: Preparation of 1R*, 2R*, βR*, γS* and 1R*, 2S*, βR*, γS* 4-((1-(4-((3-(4-Acetyl-3-hydroxy-2-propylphenoxy)propyl)thio)phenyl)-3-carbomethoxy-2-methylpropyl)thio)-gamma-hydroxy-beta-methylbenzenebutanoic acid gamma lactone To a solution of the alcohol from Step A, Example 1 (930 mg) and the thiol from Step I of this Example (410 mg) in anhydrous CH$_2$Cl$_2$ (75 ml) was added dry zinc iodide (3.13 g) and the mixture was stirred at room temperature under N$_2$ for 4.5 hours. The reaction mixture was washed with 0.1N HCl, brine, dried over Na$_2$SO$_4$ and evaporated to dryness to give an oil which was purified on a PREP-500 Waters HPLC using hexane/EtOAc (10:8) as eluant to give the title compound as an oil (700 mg), 54%.

$^1$H NMR (CDCl$_3$) delta: 0.62 (3H, d, J=6 Hz), 0.85–1.0 (6H, m), 1.15 (2H, d 1.45–1.65 (2H, m), 2.0–2.2 (2H, m), 2.2–2.4 (2H, m), 2.5–2.7 (7H, m, containing a sharp singlet), 2.7–2.9 (2H, m), 3.1 (2H, t, J=6 Hz), 3.65 and 3.7 (3H, 2 singlets), 4.05–4.2 (3H, m), 5.5 (1H, d, J=5.6 Hz), 6.45 (1H, d, J=7 Hz), 7.0–7.3 (8H, m), 7.6 (1H, d, J=7 hz), 12.7 (1H, s).

Step K: Preparation of 1R, 2R, βR, γS; 1R, 2S, βR, γS; 1S, 2R, βR, γS; 1S, 2S, βR, γS; 1R, 2R, βS, γR; 1R, 2S, βS, γR; 1S, 2R, βS, γR; 1S, 2S, βS, γR 4-((1-(4-((3-(4-Acetyl-3-hydroxy-2-propylphenoxy)propyl)thio)phenyl)-3-carboxy-2-methylpropyl)thio)-gamma-hydroxybetamethylbenzenebutanoic acid disodium salt monohydrate To a solution of the ester lactone from Step J of this Example (664 mg) in THF (10 ml) and MeOH (1 ml) was added 2N NaOH (1.2 ml) and stirred overnight at room temperature. The reaction mixture was evaporated to dryness and passed through a column of neutral XAD-8 resin eluting with water (250 ml) and then with 95% EtOH to give, after evaporation of the ethanol, the title compound as a foam (690 mg, 100%).

Analysis for: C$_{36}$H$_{42}$O$_8$S$_2$Na$_2$·H$_2$O: Calc'd: C, 59.16; H, 6.07; S, 8.77; Na, 6.29. Found: C, 59.15; H, 6.28; S, 8.98; Na, 5.40.

EXAMPLE 10

Preparation of 1R*, 2R*, βR*; 1R*, 2R*, βS*; 1R*, 2R*; and 1R*, 2S*, βS*

4-((1-(4-((3-(4-Acetyl-3-hydroxy-2-propylphenoxy)propyl)thio)phenyl)-3-carboxy-2-methylpropyl)thio)-beta-methyl-gamma-oxobenzenebutanoic acid monohydrate

Step A: Preparation of Methyl 4-((1-(4-((3-(4-acetyl-3-hydroxy-2-propylphenoxy)propyl)thio)phenyl)-4-methoxy-2-methyl-4-oxobutyl)thio)-betamethyl-gamma-oxobenzenebutanoate To a solution of alcohol from Example 1, Step A (1.6 g) and the thiol from Example 9, Step E (800 mg) in anhydrous CH$_2$Cl$_2$ (170 ml) was added dry zinc iodide (10.7 g) and stirred at room temperature under N$_2$ for 3.5 hours. The reaction mixture was washed with 0.1N HCl, brine and dried over Na$_2$SO$_4$ to give an oil which was purified on PREP-500 Waters HPLC using hexane-EtOAc (2:1) as eluant to give an oil (1.06 g, 45%).

$^1$H NMR CDCl$_3$ delta: 0.85–1.25 (9H, m), 1.45–1.65 (2H, m), 2.0–2.2 (2H, m), 2.2–2.5 (2H, m), 2.5–2.7 (7H, m, containing a sharp singlet), 2.85–3.0 (1H, q), 3.15 (2H, t, J=6 Hz), 3.63 (3H, s), 3.66 and 3.7 (3H, 2s), 3.8–3.9 (1H, m), 4.15 (2H, t, J=6 Hz), 4.35–4.45 (1H, m), 6.45 (1H, d, J=7 Hz), 7.2–7.4 (6H, m), 7.58 (1H, d, J=7 Hz), 7.75–7.85 (2H, m).

Analysis for: C$_{38}$H$_{46}$O$_8$S$_2$: Calc'd: C, 65.68; H, 6.67; S, 9.23. Found: C, 65.48; H, 6.59; S, 9.51.

Step B: Preparation of 4-((1-(4-((3-(4-Acetyl-3-hydroxy-2-propylphenoxy)propyl)thio)phenyl)-3-carboxy-2-methylpropyl)thio)-beta-methyl-gamma-oxo-benzenebutanoic acid monohydrate To a solution of ester from Step A of this Example (760 mg) in THF (15 ml) and MeOH (1 ml) was added 2N NaOH (2.4 ml) and stirred overnight at room temperature. The reaction mixture was diluted with H$_2$O (50 ml) and acidified with 2N HCl and extracted with CH₂Cl₂ (2×50 ml). The combined organic layers were washed with brine, dried over Na₂SO₄ and purified on a column of flash silica gel 230–400 mesh using toluene-dioxane-acetic acid (10:2:0.1) as eluant to give the title compound as a foam (580 mg, 79%).

Analysis for: $C_{36}H_{42}O_8S_2.H_2O$: Calc'd: C, 63.13; H, 6.47; S, 9.36. Found: C, 62.64; H. 6.25; S, 9.46.

EXAMPLE 11

Preparation of 4-((3-(4-acetyl-3-hydroxy-2-propylphenoxy)propyl)thio)-γ-((4-(3-carboxy-1-hydroxypropyl)phenyl)thio-benzene butanoic acid, disodium salt, monohydrate, mixture of isomers

Step A: Methyl 4(3-bromopropylthio)-γ-((4-(3-methoxycarbonyl-1-hydroxy-propyl)phenyl)thio)-henzenebutanoate, mixture of isomers To a cooled (0° C.) solution made of the ketone obtained in Step D of Example 2 (2.72 g) in DME (1,2-dimethoxyethane) (25 c.c.) and MeOH (5 c.c.) containing CeCl₃ (5 mg), was added portion-wise NaBH₄ (138 mg) and the mixture was kept at this temperature until the starting ketone had disappeared. The mixture was then poured into ice-cold water, acidified with 1N HCl and the organic material was extracted into ethyl acetate; the organic layer was washed with brine, dried with Na₂SO₄ and the solvents were removed in vacuo to yield an oil which was purified on silica gel to yield the title compound as an oil.

Analysis Calc'd: C, 54.05; H, 5.62; S, 11.54. Found: C, 53.83; H, 5.70; S, 11.55.

Step B: Preparation of 4-((1-(4-((3-(4-acetyl-3-hydroxy-2-propylphenoxy)-propyl)thio)phenyl)3-(methoxycarbonyl)propyl)thio)-γ-hydroxybenzenebutanoic acid, -γ-lactone, mixture of isomers A suspension of the bromide from the previous step (2.05 g), 2,4-dihydroxy-3-propylacetophenone (933 mg), and milled potassium carbonate (765 mg) in MEK (methylethylketone) (20 c.c.) was refluxed for 6 hours. Thereafter it was cooled to room temperature, the solids were filtered off and the solvent was removed in vacuo to yield an oil which was purified on silica gel to yield the title compound as an oil.

NMR ¹H-250 MHz/CDCl₃

| δ(ppm) | No. of H | m | J(Hz) |
|---|---|---|---|
| 12.75 | 1 | s | — |
| 7.58–7.62 | 1 | d | 8.3 |
| 7.15–7.3 | 8 | m | — |
| 6.4–6.48 | 1 | d | 8.3 |
| 5.4–5.5 | 1 | t | 6.0 |
| 4.1–4.25 | 3 | m | — |
| 3.65 | 3 | s | — |
| 3.1–3.18 | 2 | t | 5.0 |
| 2.05–2.7 | 15 | m | — |
| 1.5–1.6 | 2 | m | — |
| 0.9–1.0 | 3 | t | 5.0 |

Step C: Preparation of 4-((3-(4-acetyl-3-hydroxy-2-propylphenoxy)propyl)thio)-γ-((4-(3-carboxy-1-hydroxypropyl)phenyl)thio)benzene butanoic acid, disodium salt, monohydrate, mixture of isomers To a solution of the lactone from the previous step (1.64 g) in MeOH (5 c.c.) and THF (20 c.c.) was added 2N NaOH (3.9 c.c.) and the mixture was stirred for 2 hours The reaction mixture was evaporated to dryness in vacuo and absorbed onto XAD-8 neutral resin in water, washed with water and then eluted off with ethanol. Evaporation of the solvent in vacuo yielded the title compound.

Analysis Calc'd: C, 58.11; H, 5.74; S, 9.12; Na, 6.54 Found: C, 58.57; H, 5.97; S, 9.31; Na, 5.16

EXAMPLE 12

Preparation of βR*, γS* and βS*, γR* 4-((3-(4-acetyl-3-hydroxy-2-propylphenoxy)propyl)thio)-γ-((2-carboxymethyl)thio)-β-methylbenzenebutanoic acid disodium salt (mixture of diastereoisomers),

Step A: Preparation of Methyl 4-((3-(4-acetyl-3-hydroxy-2-propylphenoxy)propylthio)-γ-((-2-methoxycarbonylmethyl)thio)-β-methylbenzenebutanoate (mixture of diastereoisomers, monohydrate To an efficiently stirred solution of the alcohol (948 mg) from Step A of Example 1 and methyl thioglycolate (233 mg) in dichloroethane (10 c.c.) was added ZnI₂ (1.92 g) and the suspension was stirred for 3 hours. Thereafter, in HCl (20 c.c.), H₂O (20 c.c.) and dichloromethane (50 c.c.) were added. The organic layer was separated, washed with brine, and dried with Na₂SO₄. The solvents were removed in vacuo to yield a residue which was chromatographed on silica gel to yield the title compound as an oil.

Analysis Calc'd: C, 59.97; H, 6.94; S, 11.04. Found: C, 59.91; H, 7.09; S, 10.94.

Step B: Preparation of βR*, γS* and βS*, γR* 4-((3-(4-acetyl-3-hydroxy-2-propylphenoxy)propyl)thio)-γ-((2-carboxymethyl)thio)-β-methylbenzenebutanoic acid disodium salt, hemihydrate (mixture of diastereoisomers)

A solution of the diester from the previous step (790 mg) in 2N NaOH (2.1 c.c.), MeOH (2 c.c.) and THF (10 c.c.) was stirred for 4 hours. The reaction mixture was evaporated to dryness and absorbed onto XAD-8 neutral resin in water, washed with water and then eluted off with ethanol. Evaporation of the solvent in vacuo yielded the title compound.

Analysis Calc'd: C, 55.18; H, 5.66; S, 10.91; Na, 7.82. Found: C, 55.60; H, 5.66; S, 9.96; Na, 7.17.

EXAMPLE 13

Preparation of βR*, γR*
4-((3-(4-acetyl-3-hydroxy-2-propylphenoxy)propyl)thio)γ-((2-carboxyethyl)thio)-β-methylbenzenebutanoic acid, disodium salt, mixture of enantiomers and preparation of βR*, γS*
4-((3-(4-acetyl-3-hydroxy-2-propylphenoxy)propyl)thio)γ-((2-carboxyethyl)-thio)-β-methylbenzenebutanoic acid, disodium salt, mixture of enantiomers

Step A: Preparation of βR*, γR* 4-((3-(4-acetyl-3-hydroxy-2-propylphenoxy)propyl)thio)-γ-(thio)-β-methylbenzenebutanoic acid-γ-thiolactone, mixture of enantiomers A solution of the thioacetate obtained from Step A of Example 7 (42 g) in THF (250 c.c.) was cooled to 0° C., a solution of NaOMe (6.5 g) in MeOH (100 c.c.) was added, and the mixture was kept at 0° C. for 30 minutes. Thereafter, it was poured into ice-cold 1N HCl (200 c.c.); the organic material was extracted into ethyl acetate and the organic layer successively washed with 10% $NaHCO_3$ and brine, dried with $Na_2SO_4$ and concentrated in vacuo to yield a residue which was then dissolved in dry THF (250 c.c.) and cooled to 0° C. Thereafter, a suspension of NaH (1.6 g) in THF (50 c.c.) was added dropwise and the mixture kept at 0° C. for 6 hours. It was then poured into ice-cold 1N HCl (300 c.c.) and extracted into ethyl acetate. The organic layer was washed with 10% $NaHCO_3$, brine and then dried with $Na_2SO_4$ and concentrated in vacuo to yield a residue which was purified on silica gel to yield the mixture of the βR*, γR* and the βR*, γS* thiolactones from which the βR*, γR* lactone was purified by repetitive preparative HPLC.

Analysis Calc'd: C, 65.47; H, 6.59; S, 13.98. Found: C, 64.72; H, 6.32; S, 13.18.

NMR $^1$H-250 MHz/CDCl$_3$ for βR*, γR*

| δ(ppm) | No. of H | M | J(Hz) |
|---|---|---|---|
| 4.50 | 1 | d | 6.6 |
| 1.09 | 3 | d | 6.6 |

Step B: Preparation of βR*, γS* 4-((3-(4-acetyl-3-hydroxy-2-propylphenoxy)propyl)thio)-γ-(thio)-β-methylbenzenebutanoic acid -γ-thiolactone, mixture of enantiomers This lactone was isolated by repetitive preparative HPLC purification of the mixture of the βR*, γR* and βR*, γS* thiolactones obtained in the previous step.

Analysis Calc'd: C, 65.47; H, 6.59; S, 13.98. Found: C, 64.69; H, 6.03; S, 13.48.

NMR $^1$H-250 MHz/CDCl$_3$ for βR*, γS*

| δ(ppm) | No. of H | M | J(Hz) |
|---|---|---|---|
| 5.0 | 1 | d | 6.6 |
| 0.8 | 3 | d | 6.6 |

Step C: Preparation of βR*, γR* methyl 4-((3-(4-acetyl-3-hydroxy-2-propylphenoxy)propyl)thio)-γ-((2-methoxycarbonylethyl)thio)-β-methylbenzenebutanoate, mixture of enantiomers To an ice cold solution of Na (19 mg) in MeOH (5 c.c.) was added a THF (5 c.c.) solution of the lactone (290 mg) obtained in Step A of this Example and the mixture was reacted at 0° C. for 1 hour. Methyl 3-bromopropionate (127 mg) was then added and reacted for 2 hours at 0° C. Dowex 50-WX-8 resin was then added and stirred for 15 minutes and removed by filtration. The filtrate was concentrated in vacuo, then diluted with $CH_2Cl_2$ (15 c.c.), washed with brine and the organic layer was dried with $Na_2SO_4$. Removal of the solvents in vacuo, followed by purification of the residue on silica gel yielded the title compound as an oil.

Analysis Calc'd: C, 62.47; H, 6.99; S, 11.12. Found C, 62.44; H, 7.67; S, 10.70.

Step D: Preparation of βR*, γS* methyl 4-((3-(4-acetyl-3-hydroxy-2-propylphenoxy)propyl)thio)-γ-((2-methoxycarbonylethyl)thio)-β-methylbenzenebutanote mixture of enantiomers To an ice cold solution of Na (28 mg) in MeOH (10 c.c.) was added a THF (10 c.c.) solution of the lactone (430 mg) obtained in Step B of this Example and the mixture was reacted for 1 hour at 0° C. Methyl 3-bromopropionate (200 mg) was then added and reacted for 2 hours. Dowex 50-WX-8 resin was then added, stirred for 15 minutes and removed by filtration. The filtrate was concentrated in vacuo, diluted in $CH_2Cl_2$ (25 c.c.), washed with brine and the organic layer was dried with $Na_2SO_4$. Removal of the solvent in vacuo, followed by purification of the residue on silica gel yielded the title compound as an oil.

Analysis Calc'd: C, 62.47; H, 6.99; S, 11.12. Found: C, 62.51; H, 7.04; S, 11.05.

Step E: Preparation of βR*, γR* 4-((3-(4-acetyl-3-hydroxy-2-propylphenoxy)propyl)thio)-γ-((2-carbomyethyl) thio)-β-methylbenzenebutanoic acid, disodium salt, mixture of enantiomers To a solution of the product obtained in Step C of this Example (231 mg) in MeOH (5 c.c.), THF (5 c.c.) and $H_2O$ (2 c.c.) was added 2N NaOH (0.6 c.c.) and the mixture was stirred at room temperature for 12 hours. The solvents were then removed in vacuo and the residue absorbed on XAD-8 neutral resin in water, washed with water and then eluted off with ethanol. Evaporation of the solvent in vacuo yielded the title compound as a highly hygroscopic foam.

NMR $^1$H-250 MHz/CD$_3$OD

| δ(ppm) | No. of H | m | J(Hz) |
|---|---|---|---|
| 7.59–7.64 | 1 | d | 8.3 |
| 7.12–7.21 | 4 | m | |
| 6.41–6.45 | 1 | d | 8.3 |
| 4.0–4.1 | 2 | t | 5.5 |
| 3.59–3.65 | 1 | d | 8.3 |
| 2.97–3.05 | 2 | t | 5.5 |
| 1.65–2.55 | 14 | m | |
| 1.35–1.45 | 2 | m | |
| 0.9–1.0 | 3 | d | 6.1 |
| 0.75–0.82 | 3 | t | 5.5 |

Step F: Preparation of βR*, γS 4-((3(4-acetyl-3-hydroxy-2-propylphenoxy)propyl)thio)-γ-((2-carboxyethyl)thio)-β-methyl benzenebutanoic acid, disodium salt, mixture of enantiomers To a solution of the product obtained in Step D of this Example (387 mg) in MeOH (5 c.c.), THF (5 c.c.) and H$_2$O (2 c.c.) was added 2N NaOH (1.0 c.c.) and the mixture was stirred at room temperature for 12 hours. The solvents were then removed in vacuo and the residue absorbed on XAD-8 neutral resin in water, washed with water and then eluted off with ethanol. Evaporation of the solvent in vacuo yielded the title compound as a highly hygroscopic foam.

NMR $^1$H-250 MHZ/CD$_3$OD

| δ(ppm) | No. of H | m | J(Hz) |
|---|---|---|---|
| 7.59–7.65 | 1 | d | 8.3 |
| 7.12–7.22 | 4 | m | |
| 6.41–6.45 | 1 | d | 8.3 |
| 4.0–4.1 | 2 | t | 5.5 |
| 3.59–3.65 | 1 | d | 8.3 |
| 2.95–3.05 | 2 | t | 5.5 |
| 1.65–2.55 | 14 | m | |
| 1.35–1.45 | 2 | m | |
| 0.75–0.85 | 3 | t | 5.5 |
| 0.69–0.75 | 3 | d | 6.1 |

EXAMPLE 14

Preparation of βR*, γS* 4-((3-(4-acetyl-3-hydroxy-2-propylphenoxy)propyl)sulfonyl)-γ-((2-carboxyethyl)thio)-β-methylbenzenebutanoic acid, disodium salt, mixture of enantiomers, monohydrate

Step A: Preparation of βR*, γS* 4-((3-hydroxy-2-propylphenoxy)propyl)sulfonyl)-γ-(thio)-β-methylbenzene butanoic acid, -γ-thiolactone, mixture of enantiomers To a cooled (0° C.) solution of the lactone (230 mg) obtained in Step B of Example 13 in chloroform (5 c.c.) was added m-chloroperoxybenzoic acid (m-CPBA) (105 mg) and the suspension was stirred at 0° C. for 45 minutes. Another portion (10.5 mg) of m-CPBA was then added and reacted for 1 hour at 0° C. The suspension was warmed up to room temperature and Ca(OH)$_2$ (111 mg) was added and the mixture stirred for 1 hour. Insolubles were then filtered off and the filtrate concentrated to dryness to yield the title compound.

Analysis Calc'd.1H$_2$O: C, 59.22; H, 6.34; S, 12.61. Found: C, 59.24, H, 5.87; S, 12.43.

Step B: Preparation of βR*, γS* methyl 4-((3-(4-acetyl-3-hydroxy-2-propylphenoxy)propyl)sulfonyl)-γ-((2-methoxycarbonyl ethyl)thio)-β-methylbenzenebutanoate, mixture of enantiomers To a cooled (0° C.) solution of the lactone obtained in the previous step (800 mg) in MeOH (25 c.c.) was added NaOMe (110 mg) followed, one-half hour later, by methyl acrylate (215 mg). After 45 minutes at this temperature, 1N HCl (25 c.c.) was added and most of the methanol removed in vacuo; organic materials were extracted into ethyl acetate (3×25 c.c.), the organic layer washed with brine, dried with Na$_2$SO$_4$ and concentrated to dryness to yield a residue which was purified by chromatography on silica gel, yielding the title compound as an oil.

Analysis Calc'd: C, 59.19; H, 6.62; S, 10.53. Found: C, 58.74; H, 6.56; S, 9.60.

Step C: Preparation of βR*, γS* 4-((3-(4-acetyl-3-hydroxy-2-propylphenoxy)propyl)sulfonyl)-γ-((2-carboxyethyl)thio)-β-methylbenzenebutanoic acid, disodium salt, mixture of enantiomers, monohydrate To a cooled (0° C.) solution of the compound obtained in the previous step (925 mg) in THF (10 c.c.) and MeOH (5 c.c.) was added 2N NaOH (2.3 c.c.) and the mixture was stirred for 48 hours while being warmed up to room temperature. The solvents were then removed in vacuo and the residue absorbed on XAD-8 neutral resin in water, washed with water and then eluted off with ethanol. Removal of the solvent from the ethanolic fraction yielded the title compound as a foam.

Analysis Calc'd.1H$_2$O: C, 52.53; H, 5.65; S, 9.98 Found: C, 52.31; H, 5.43; S, 9.45.

EXAMPLE 15

Preparation of βR*, γS* and βR*, γR* 4-((3-(4-acetyl-3-hydroxy-2-propylphenoxy)propyl)thio)-γ-((2-N,N-dimethylcarbonylethyl)thio)-β-methylbenzenebutanoic acid, sodium salt

Step A: Preparation of βR*, γS* and βR*, γR* methyl 4-((3-(4-acetyl-3-hydroxy-2-propylphenoxy)propyl)thio)-γ-((2-N,N-dimethylcarbonylethyl)thio)-β-methylbenzenebutanoate To a cooled (0° C.) solution of the mixture of the lactones prepared in Step A of Example 13 (916 mg) in MeOH (20 c.c.) and THF (10 c.c.) was added NaOMe (130 mg) followed 90 minutes later by N,N-dimethylacrylamide (300 mg) and this mixture was reacted for 2 hours at 0° C. It was then acidified with 1N HCl and extracted with ethyl acetate (3×25 c.c.); the organic layer was washed with brine, dried with Na$_2$SO$_4$ and concentrated to yield a residue which was purified on silica gel to yield the title compound as an oil.

Analysis Calc'd: C, 63.13; H, 7.35; S, 10.87 Found: C, 62.86; H, 7.58; S, 10.83.

Step B: Preparation of βR*, γS* and βR*, γR* 4-((3-(4-acetyl-3-hydroxy-2-propylphenoxy)propyl)thio)-γ-((2-N,N-dimethylcarbonylethyl)thio)-β-methylbenzenebutanoic acid, sodium salt To a solution of the ester obtained in the previous step (590 mg) in MeOH (10 c.c.) and H$_2$O (2 c.c.) was added 2N NaOH (1.5 c.c.) and the mixture was reacted for 12 hours. It was then acidified and extracted with ethyl acetate (3×25 c.c.); the organic layer was washed with brine, dried with Na$_2$SO$_4$ and concentrated to dryness. To the residue (512 mg) dissolved in EtOH (5 c.c.) and MeOH (5 c.c.) was added 1N NeOH (0.890 c.c.) and the obtained solution was evaporated to dryness in vacuo to yield the title compound as a foam.

Analysis Calc'd: C, 60.28; H, 6.75; S, 10.73. Found: C, 60.02; H, 6.75; S, 10.78.

What is claimed is:

1. A compound of the formula:

(I)

[structural formula]

[structural formula]

wherein:
each R is independently H, OH, lower alkyl, lower alkenyl, trifluoromethyl, lower alkoxy; phenyl, phenyl substituted by alkyl of 1 to 3 carbon atoms or by halogen, benzyl, phenethyl, halogen, $N(R^4)_2$, $-(C=O)R^1$, $CH_2OR^4$, CN, $SR^{10}$, $SOR^{10}$, $SO_2R^{10}$, or nitro;
$R^1$ is H, lower alkyl, or lower alkoxy;
$R^2$ is H, lower alkyl, $R^4CO$, or $R^4OCH_2$;
each $R^3$ is independently lower alkyl or lower alkenyl;
each $R^4$ is independently H or lower alkyl;
each $R^5$ is independently H, $OR^2$, lower alkyl, or both $R^5$'s may be combined to create a doubly bonded oxygen (=O) or a $=C(R^4)_2$ group;
each $R^6$ is independently H, OH, or lower alkyl;
each $R^7$ is independently $COOR^4$ or tetrazolyl;
$R^9$ is $R^3$, $-(C)_b-R^7$ with $R^5$, $R^5$, $-CH_2-CH(NH_2)-C(O)-Y^1$,

[structural formula]

[structural formula]

-continued

[structural formula] $-(CH_2)_a-R^7$;

each $R^{10}$ is independently OH; $N(R^4)_2$; $CF_3$; lower alkyl; lower alkoxy; phenyl; or phenyl substituted by one or more alkyl or alkoxy groups of 1 to 3 carbon atoms, halogen, hydroxy, $COOR^4$, CN, formyl or lower alkylacyl;
$R^{13}$ is H or $R^{10}$;
$X^1$, $X^2$ and $X^3$ are each independently O, S, SO, $SO_2$, $S(O)=NR^4$, $NR^4$, $NCOR^1$, NCN, or $NCONHR^4$;
$Y^1$ is OH or the N-terminus of an amino acid such that $Y^1H$ is an essential amino acid:
Z is O, H and OH, or H and $R^4$;
each a is independently 0 to 4;
each b is independently 1 to 6;
each n is independently 0 to 6;
each q is independently 0 to 4;
each r is independently 0 to 4;
each t is independently 0 to 1;
or the pharmaceutically acceptable salts thereof, with the proviso that at least one $R^7$ is COOH or tetrazolyl and that when $R^7$ is COOH then:
R is not CN;
$R^1$ is not lower alkoxy; and
$R^{10}$ is not lower alkoxy or phenyl substituted by CN or $COOR^4$ but may be carboxyphenyl.

2. A compound according to claim 1, wherein
$R^1$ is H or lower alkyl;
$R^2$ is H;
each $R^5$ is independently H; $OR^2$; or both $R^5$'s may be combined to create a doubly bonded oxygen (=O);
each $R^7$ is independently $COOR^4$; CHO; $CH_2OH$; or tetrazole;
$X^1$, $X^2$ and $X^3$ are each independently O, S, SO or $SO_2$;
each n is independently 1 or 2;
or the pharmaceutically acceptable salts thereof.

3. A compound according to claim 2, wherein
each R is independently H; OH; lower alkyl; trifluoromethyl; lower alkoxy; halogen; $N(R^4)_2$; $-(C=O)R^1$; $CH_2OR^4$; $SR^{10}$; $SOR^{10}$; or $SO_2R^{10}$;
$R^1$ is lower alkyl;
each n is 1; q=0;
or the pharmaceutically acceptable salts thereof.

4. A compound according to claim 3, of the formula:

(II)

[structural formula]

wherein $R^9$ is

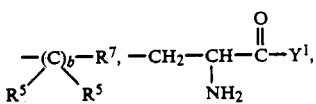

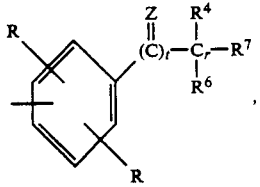

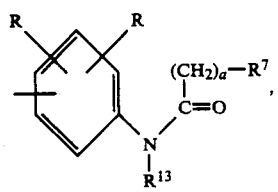

or,

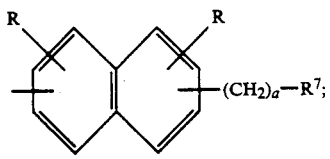

$R^{14}$ is $COOR^4$; u is 0 to 4;

or the pharmaceutically acceptable salts thereof.

5. A compound according to claim 1, which is:

4-((1-(4-((3-(4-acetyl-3-hydroxy-2-propylphenoxy)-propyl)thio)phenyl)-3-carboxypropyl)thio)-gamma-oxobenzenebutanoic acid;

4-((3-(4-acetyl-3-hydroxy-2-propylphenoxy)propyl)-thio)-gamma-((3-(carboxyacetyl)amino)-phenyl)thio-beta-methylbenzenebutanoic acid;

4-((1-(4-((3-(4-acetyl-3-hydroxy-2-propylphenoxy)-propyl)thio)phenyl)-3-carboxypropyl)thio)-beta-methyl-gamma-oxobenzenebutanoic acid;

N(S(γ-(4-((3-(4-acetyl-3-hydroxy-2-propylphenoxy)-propyl)thio)phenyl)-gamma-carboxy-β-methyl-propyl)cysteinyl)glycine disodium salt;

4-((3-(4-acetyl-3-hydroxy-2-propylphenoxy)propyl)-thio)-gamma-((2-carboxyethyl)thio)-beta-methyl-benzenebutanoic acid disodium salt;

4-((3-(4-acetyl-3-hydroxy-2-propylphenoxy)propyl)-thio)-gamma-(butylthio)-beta-methylbenzenebutanoic acid;

4-((3-(4-acetyl-3-hydroxy-2-propylphenoxy)propyl)-thio)-beta-methyl-gamma-((1H-tetrazole-5-yl-methyl)thio)benzenebutanoic acid disodium salt monohydrate;

methyl 4-((3-(4-acetyl-3-hydroxy-2-propylphenoxy)-propyl)thio)-beta-methyl-gamma-((1H-tetrazole-5-yl-methyl)thio)benzenebutanoate sodium salt;

4-((1-(4-((3-(4-acetyl-3-hydroxy-2-propylphenoxy)-propyl)thio)phenyl)-3-carboxy-2-methylpropyl)-thio)-gamma-hydroxy-beta-methylbenzenebutanoic acid disodium salt monohydrate;

4-((1-(4-((3-(4-acetyl-3-hydroxy-2-propylphenoxy)-propyl)thio)phenyl)-3-carboxy-2-methylpropyl)-thio)-beta-methyl-gamma-oxobenzenebutanoic acid monohydrate;

4-((3-(4-acetyl-3-hydroxy-2-propylphenoxy)propyl)-thio)-γ-((4-(3-carboxy-1-hydroxypropyl)-phenyl)thio-benzene butanoic acid, disodium salt, monohydrate;

4-((3-(4-acetyl-3-hydroxy-2-propylphenoxy)propyl-thio)-γ-((2-carboxymethyl)thio)-β-methylbenzenebutanoic acid disodium salt, hemihydrate;

4-((3-(4-acetyl-3-hydroxy-2-propylphenoxy)propyl)-thio)-γ-((2-carboxyethyl)thio)-β-methylbenzenebutanoic acid, disodium salt;

4-((3-(4-acetyl-3-hydroxy-2-propylphenoxy)propyl)-sulfonyl-γ-((2-carboxyethyl)thio)-β-methylbenzenebutanoic acid, disodium salt, monohydrate; or 4-((3-(4-acetyl-3-hydroxy-2-propylphenoxy)-propyl)thio-γ-((2-N,N-dimethylcarbonylethyl)thio)-β-methylbenzenebutanoic acid, sodium salt.

6. A pharmaceutical composition useful in antagonizing leukotriene action in mammals comprising an amount of a compound of claim 1 effective as a leukotriene antagonist and a pharmaceutically acceptable carrier.

7. A method of preventing the synthesis, the action or the release of SRS-A and the leukotrienes $C_4$, $D_4$, $E_4$ and $B_4$ in mammals, which comprises administering to said mammal an effective amount of a compound of claim 1.

8. The method of claim 7 wherein SRS-A, and leukotrienes $C_4$, $D_4$, and $E_4$ are affected.

9. The method of claim 7 wherein leukotriene $B_4$ is affected.

* * * * *